(12) United States Patent
Nagel et al.

(10) Patent No.: US 9,056,833 B2
(45) Date of Patent: Jun. 16, 2015

(54) CRYSTALLINE PHASES OF 2'-{[2-(4-METHOXY-PHENYL)-ACETYLAMINO]-METHYL}-BIPHENYL-2-CARBOXYLIC ACID (2-PYRIDIN-3-YL-ETHYL)-AMIDE

(75) Inventors: Norbert Nagel, Frankfurt am Main (DE); Harald Berchtold, Frankfurt am Main (DE); Michael Schur, Frankfurt am Main (DE); Dirk Hoerstermann, Paris (FR)

(73) Assignee: SANOFI-AVENTIS DEUTSCHLAND GMBH, Frankfurt (DE)

( * ) Notice: Subject to any disclaimer, the term of this patent is extended or adjusted under 35 U.S.C. 154(b) by 100 days.

(21) Appl. No.: 13/375,363

(22) PCT Filed: May 26, 2010

(86) PCT No.: PCT/EP2010/057273
§ 371 (c)(1),
(2), (4) Date: Nov. 30, 2011

(87) PCT Pub. No.: WO2010/139585
PCT Pub. Date: Dec. 9, 2010

(65) Prior Publication Data
US 2012/0071520 A1 Mar. 22, 2012

Related U.S. Application Data

(60) Provisional application No. 61/306,222, filed on Feb. 19, 2010.

(30) Foreign Application Priority Data

Jun. 3, 2009 (EP) .................................... 09007330

(51) Int. Cl.
C07D 213/40 (2006.01)
A61K 31/4406 (2006.01)
C07D 213/16 (2006.01)

(52) U.S. Cl.
CPC ............ *C07D 213/40* (2013.01); *C07D 213/16* (2013.01)

(58) Field of Classification Search
None
See application file for complete search history.

(56) References Cited

U.S. PATENT DOCUMENTS

| 6,531,495 | B1 | 3/2003 | Brendel et al. |
| 2007/0043091 | A1 | 2/2007 | Wirth |

FOREIGN PATENT DOCUMENTS

| RU | 2 252 214 C2 | 5/2005 |
| WO | 01/25189 A1 | 4/2001 |
| WO | 2005/084675 A1 | 9/2005 |
| WO | 2007/124849 A2 | 11/2007 |
| WO | 2007/124849 A3 | 11/2007 |

OTHER PUBLICATIONS

Caira, Mino R., "Crystalline Polymorphism of Organic Compounds," Topics in Current Chemistry (1998), vol. 198, pp. 163-208.
International Search Report dated Mar. 21, 2011 issued in PCT/EP2010/057273.
Hirayama, N., Handbook for forming crystal, 2008, pp. 10-11, 57-65.
Japanese Notification of Reasons for Refusal issued in Japanese Patent Application No. 2012-513545 dated Jun. 3, 2014.
Nagase, H., The Practice of Medicinal Chemistry, 1999, Second Volume, p. 452-3.
Russian Decision on grant of patent for invention issued in Russian Application No. 2011151399/04(077144) dated Sep. 4, 2014.
Russian Office Action issued in Russian Application No. 2011151399/04(077144) dated Apr. 7, 2014.
Yamano, M., Separation Technique, 2003, vol. 33, No. 6, pp. 25(379)-31(385).

*Primary Examiner* — Alicia L Otton
(74) *Attorney, Agent, or Firm* — Morrison & Foerster LLP

(57) ABSTRACT

The present invention relates to polymorphic forms and solvates of 2'-{[2-(4-methoxy-phenyl)-acetylamino]-methyl}-biphenyl-2-carboxylic acid (2-pyhdin-3-yl-ethyl)-amide, processes for their preparation and their use, in particular for the preparation of medicaments.

8 Claims, 19 Drawing Sheets

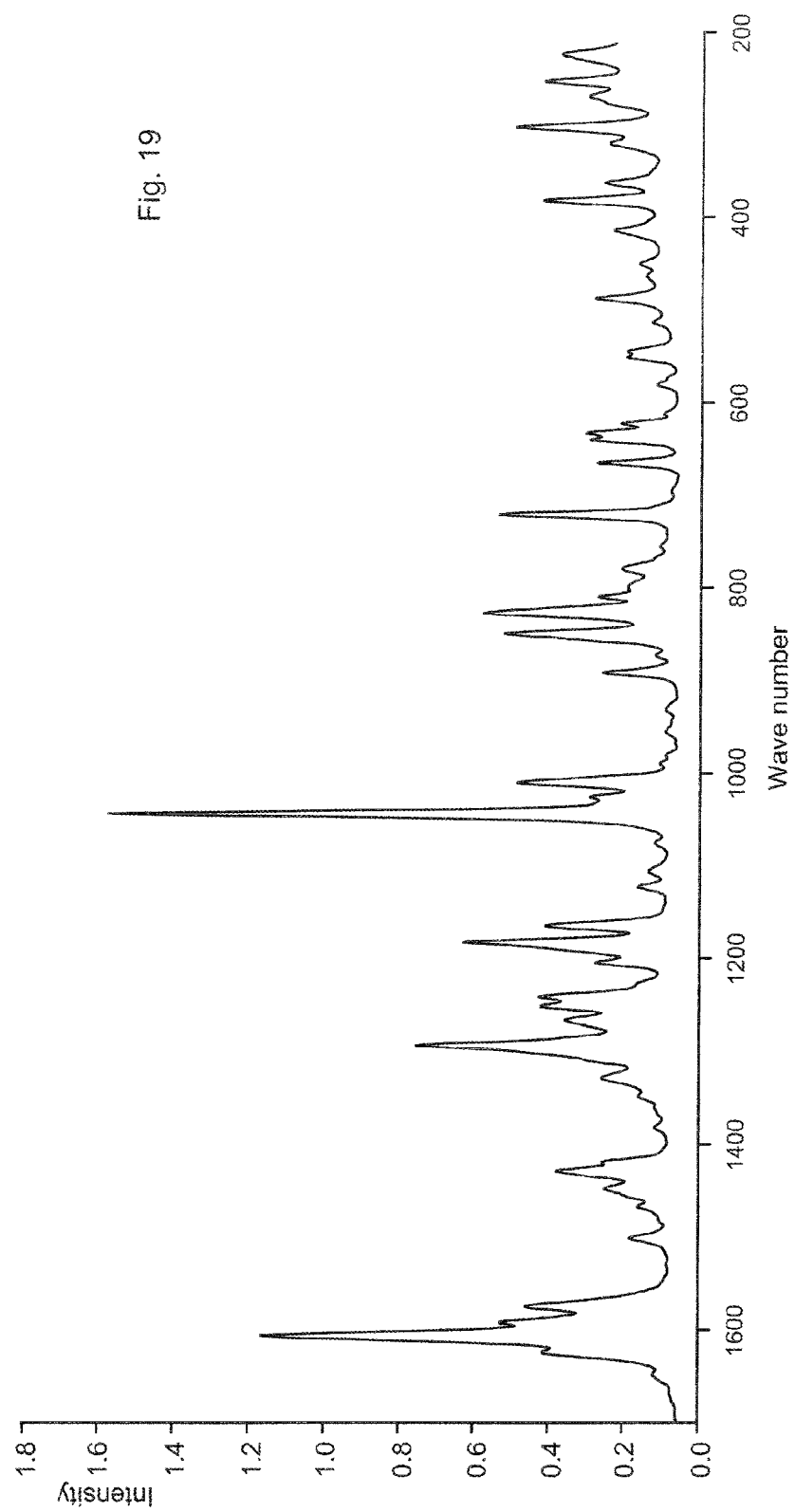

CRYSTALLINE PHASES OF 2'-{[2-(4-METHOXY-PHENYL)-ACETYLAMINO]-METHYL}-BIPHENYL-2-CARBOXYLIC ACID (2-PYRIDIN-3-YL-ETHYL)-AMIDE

The present invention relates to polymorphic forms and solvates of 2'-{[2-(4-methoxy-phenyl)-acetylamino]-methyl}-biphenyl-2-carboxylic acid (2-pyridin-3-yl-ethyl)-amide, processes for their preparation and their use, in particular for the preparation of medicaments.

2'-{[2-(4-Methoxy-phenyl)-acetylamino]-methyl}-biphenyl-2-carboxylic acid (2-pyridin-3-yl-ethyl)-amide of the formula I,

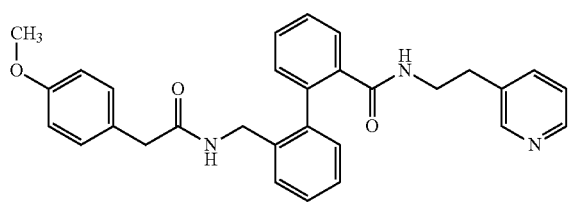

I which is also designated as AVE0118 and herein is also abbreviated as "compound I", is a known pharmaceutical active compound which is described in WO 01/25189, U.S. Pat. No. 6,531,495 and WO 2007/124849, for example. However, data concerning polymorphic forms, or crystalline forms, and solvates of said compound are not disclosed in the prior art.

Polymorphism is the ability of a single compound to exist in more than one form or crystal structure. Different polymorphs represent distinct solids sharing the same molecular formula, yet each polymorph may have distinct physical properties. A single compound may give rise to a variety of polymorphic forms wherein each form has different and distinct physical properties, such as different solubility profiles, different thermodynamic stability, different crystallization behavior, different filtrability, different melting point temperatures and/or different X-ray diffraction peaks. The difference in the physical properties of different polymorphic forms results from different orientation and intermolecular interactions of adjacent molecules in the solid. Polymorphic forms of a compound can be distinguished by X-ray diffraction and by other methods such as, infrared spectroscopy or Raman spectroscopy, for example. These statements apply likewise to solvates, i.e. solid addition compounds with a solvent.

However, as acknowledged by the person skilled in the art, the presence of new solid polymorphic forms or solvates of a known chemical compound cannot be foreseen. Neither the existence of crystalline phases or solvates nor the number of polymorphic forms can be foreseen. Also the conditions under which crystallization takes place to give a specific form, and the characteristics of the polymorphic forms and solvates cannot be predicted. Since properties such as the solubility and stability and consequently the suitability for use and storage of each polymorph and solvate may vary, identifying the existence of polymorphs is essential for providing pharmaceuticals with increased storage stability or predicable solubility profiles. Thus, it is desirable to investigate all solid state forms of a drug substance, including all polymorphic forms.

Accordingly, it was the object of the present invention to provide new solid forms of 2'-{[2-(4-methoxy-phenyl)-acetylamino]-methyl}-biphenyl-2-carboxylic acid (2-pyridin-3-yl-ethyl)-amide, in particular forms which have a favorable property profile or are useful in the preparation of the compound. This object was solved by providing polymorphic forms and solvates of 2'-{[2-(4-methoxy-phenyl)-acetylamino]-methyl}-biphenyl-2-carboxylic acid (2-pyridin-3-yl-ethyl)-amide which are selected from the group consisting of polymorph 1, polymorph 2, polymorph 3, a chloroform solvate, a toluene solvate and a 1,2-dichlorobenzene solvate, and any mixture thereof, which polymorphic forms and solvates have favorable properties with respect to stability, solubility, processability, hygroscopicity, flowability, filtrability or crystallization rate, for example. The form of 2'-{[2-(4-methoxy-phenyl)-acetylamino]-methyl}-biphenyl-2-carboxylic acid (2-pyridin-3-yl-ethyl)-amide which is described in the above-mentioned documents WO 01/25189, U.S. Pat. No. 6,531,495, US 2007/0043091 and WO 2007/124849, is designated herein as polymorph 4.

In the context of the present invention, polymorph, polymorphic form, solvate etc. always refers to a polymorph, polymorphic form or solvate of 2'-{[2-(4-methoxy-phenyl)-acetylamino]-methyl}-biphenyl-2-carboxylic acid (2-pyridin-3-yl-ethyl)-amide. The terms "polymorph" and "phase" may be used interchangeable herein. All data used to characterize the polymorphic forms and solvates of the present invention were obtained as outlined in the Examples provided below.

One aspect of the present invention relates to a form of 2'-{[2-(4-methoxy-phenyl)-acetylamino]-methyl}-biphenyl-2-carboxylic acid (2-pyridin-3-yl-ethyl)-amide which is selected from the group consisting of polymorph 1, polymorph 2, polymorph 3 and any mixture thereof.

Another aspect of the present invention relates to polymorph 1 of 2'-{[2-(4-methoxy-phenyl)-acetylamino]-methyl}-biphenyl-2-carboxylic acid (2-pyridin-3-yl-ethyl)-amide which has at least one property of (a) characteristic reflections in an X-ray powder diffractogram using $CuK_{\alpha 1}$ radiation in transmission mode at a 2θ angle [°] of 6.7±0.2 (intensity: medium), 13.2±0.2 (medium), 17.6±0.2 (medium), 19.1±0.2 (medium), 20.0±0.2 (strong), 21.4±0.2 (strong), 22.5±0.2 (medium); and/or (b) characteristic signals in an FT (Fourier-Transformation) Raman spectrum using a near infrared laser (λ=1064nm) at 3050±2cm$^{-1}$, 2929±2cm$^{-1}$, 2887±2cm$^{-1}$, 1605±2cm$^{-1}$, 1293±2cm$^{-1}$, 1042±2cm$^{-1}$ In one embodiment of the invention, polymorph 1 has the above property (a), in another embodiment the above property (b), in another embodiment both above properties (a) and (b). In further embodiments, polymorph 1 is also characterized by one or more of the following features.

Polymorph 1 may also be characterized by its X-ray powder diffraction pattern such as the one shown in FIG. 1 which has been obtained using $CuK_{\alpha 1}$ radiation in transmission mode, wherein the intensities of the reflections depicted in the Figure as well as those of the reflections specified above are not a prerequisite, but may vary, and represent another embodiment of the invention.

Polymorph 1 may also be characterized by the FT Raman spectrum shown in FIGS. 8, 12 and 16 which has been obtained using a near infrared laser (λ=1064 nm).

Polymorph 1 may also be characterized by its melting characteristics such as its melting point with a DSC onset temperature of 115.5±1° C. (heating rate 10° C./minute).

Polymorph 1 may also be characterized by its crystal parameters which have been determined by single crystal structure analysis. The polymorph crystallizes in the monoclinic space group P2$_1$/c with one molecule in the asymmetric unit (z=4, a=11.31±0.01Å, b=8.44±0.01Å, c=26.86±0.01 Å, β=101.80±0.01°, V=2510.5 Å$^3$, ρ=1.269Mgm$^{-3}$; at room temperature). Within the crystal structure, the molecule forms an intramolecular hydrogen bond N—H . . . O=C, and the molecules also form intermolecular hydrogen bonds which connect the molecules to chains parallel to the crystallographic b-axis.

Polymorph 1 may also be characterized by its DSC thermogram or its DVS water vapor sorption and desorption isotherms.

Polymorph 1 is thermodynamically stable below 90° C. and thus also at room temperature. Therefore, in comparison to the other known polymorphs, this polymorph is particularly suitable when a high stability is desired. It is the only polymorph that can be stored in different environments below 90° C. without the risk of transformation into another known phase. Therefore, polymorph 1 is in particular suitable for the preparation of medicaments and pharmaceutical compositions with improved stability, in particular storage stability.

Another aspect of the present invention relates to polymorph 2 of 2'-{[2-(4-methoxy-phenyl)-acetylamino]-methyl}-biphenyl-2-carboxylic acid (2-pyridin-3-yl-ethyl)-amide which has at least one property of (a) characteristic reflections in an X-ray powder diffractogram using CuK$_{α1}$ radiation in transmission mode at a 2θ angle [°] of 6.3±0.2 (intensity: medium), 8.7±0.2 (medium), 12.6±0.2 (medium), 16.4±0.2 (strong), 17.3±0.2 (medium), 19.3±0.2 (medium), 19.8±0.2 (medium); and/or (b) characteristic signals in an FT (Fourier-Transformation) Raman spectrum using a near infrared laser (λ=1064nm) at 3054±2cm$^{-1}$, 2946±2cm$^{-1}$, 1604±2cm$^{-1}$, 1294±2cm$^{-1}$, 1044±2cm$^{-1}$ In one embodiment of the invention, polymorph 2 has the above property (a), in another embodiment the above property (b), in another embodiment both above properties (a) and (b). In further embodiments, polymorph 2 is also characterized by one or more of the following features.

Polymorph 2 may also be characterized by its X-ray powder diffraction pattern such as the one shown in FIG. 2 which has been obtained using CuK$_{α1}$ radiation in transmission mode, wherein the intensities of the reflections depicted in the Figure as well as those of the reflections specified above are not a prerequisite, but may vary, and represent another embodiment of the invention.

Polymorph 2 may also be characterized by the FT Raman spectrum shown in FIGS. 9, 13 and 17 which has been obtained using a near infrared laser (λ=1064 nm).

Polymorph 2 may also be characterized by its melting characteristics such as its melting point with a DSC onset temperature of 117.2±1° C. (heating rate 10° C./minute).

Polymorph 2 may also be characterized by its lattice constants which have been determined by indexing of the X-ray powder diffraction pattern (monoclinic, a=8.75±0.01Å, b=27.96±0.01Å, c=11.09±0.01 Å, β=102.26±0.01°, V=2651.2 Å$^3$ at room temperature).

Polymorph 2 may also be characterized by its DSC thermogram or its DVS water vapor sorption and desorption isotherms.

Polymorph 2 is metastable at any temperature. Its advantage compared to other polymorphs is its higher solubility.

Another aspect of the present invention relates to polymorph 3 of 2'-{[2-(4-methoxy-phenyl)-acetylamino]-methyl}-biphenyl-2-carboxylic acid (2-pyridin-3-yl-ethyl)-amide which has at least one property of (a) characteristic reflections in an X-ray powder diffractogram using CuK$_{α1}$ radiation in transmission mode at a 2θ angle [°] of 9.0±0.2(medium), 15.5±0.2(medium), 16.8±0.2(medium), 20.3±0.2(medium), 21.0±0.2(strong), 25.6±0.2(medium); and/or (b) characteristic signals in an FT (Fourier-Transformation) Raman spectrum using a near infrared laser (λ=1064nm) at 3047±2cm$^{-1}$, 2935±2cm$^{-1}$, 1601±2cm$^{-1}$, 1293±2cm$^{-1}$, 1042±2cm$^{-1}$ In one embodiment of the invention, polymorph 3 has the above property (a), in another embodiment the above property (b), in another embodiment both above properties (a) and (b). In further embodiments, polymorph 3 is also characterized by one or more of the following features.

Polymorph 3 may also be characterized by its X-ray powder diffraction pattern such as the one shown in FIG. 3 which has been obtained using CuK$_{α1}$ radiation in transmission mode, wherein the intensities of the reflections depicted in the Figure as well as those of the reflections specified above are not a prerequisite, but may vary, and represent another embodiment of the invention.

Polymorph 3 may also be characterized by the FT Raman spectrum shown in FIGS. 10, 14 and 18 which has been obtained using a near infrared laser (λ=1064 nm).

Polymorph 3 may also be characterized by its melting characteristics such as its melting point with a DSC onset temperature of 121.7±1° C. (heating rate 10° C./minute).

Polymorph 3 may also be characterized by its crystal parameters which have been determined by single crystal structure analysis. The polymorph crystallizes in the monoclinic space group P2$_1$/c (z=4, a=8.81±0.01Å, b=15.24±0.01Å, c=20.11±0.01 Å, β=102.22±0.01°, V=2637.7 Å$^3$, ρ=1.208Mgm$^{-3}$; at room temperature).

Polymorph 3 may also be characterized by its DSC thermogram or its DVS water vapor sorption and desorption isotherms.

Polymorph 3 is thermodynamically most stable above 90° C. to 122° C. It is only metastable below 90° C. It can easily be obtained by crystallization already at elevated temperatures and is suitable for the isolation and purification of crude compound I.

The present invention further relates to polymorph 4 of 2'-{[2-(4-methoxy-phenyl)-acetylamino]-methyl}-biphenyl-2-carboxylic acid (2-pyridin-3-yl-ethyl)-amide which has at least one property of (a) characteristic reflections in an X-ray powder diffractogram using CuK$_{α1}$ radiation in transmission mode at a 2θ (2theta) angle [°] of 6.4±0.2(intensity: medium), 12.0±0.2 (medium), 13.6±0.2(strong), 18.5±0.2(medium), 18.9±0.2 (strong), 21.7±0.2(medium), 22.4±0.2(medium), 27.2±0.2 (medium); and/or (b) characteristic signals in an FT (Fourier-Transformation) Raman spectrum using a near infrared laser (λ=1064nm) at 3055±2cm$^{-1}$, 2923±2cm$^{-1}$, 1606±2cm$^{-1}$, 1044±2cm$^{-1}$ In one embodiment, polymorph 4 has the above property (a), in another embodiment the above property (b), in another embodiment both above properties (a) and (b). In further embodiments, polymorph 4 is also characterized by one or more of the following features.

Polymorph 4 may also be characterized by its X-ray powder diffraction pattern such as the one shown in FIG. 4 which has been obtained using CuK$_{α1}$ radiation in transmission mode, wherein the intensities of the reflections depicted in the Figure as well as those of the reflections specified above are not a prerequisite, but may vary, and represent another embodiment of the invention.

Polymorph 4 may also be characterized by the FT Raman spectrum shown in FIGS. 11, 15 and 19 which has been obtained using a near infrared laser (λ=1064 nm).

Polymorph 4 may also be characterized by its melting characteristics such as its melting point with a DSC (differential scanning calorimetry) onset temperature of 118.2±1° C. (heating rate 10° C./minute).

Polymorph 4 may also be characterized by its crystal parameters which have been determined by single crystal structure analysis. The polymorph crystallizes in the triclinic space group P-1 with one molecule in the asymmetric unit (z=2, a=8.38±0.01Å, b=11.15±0.01Å, c=13.97±0.01 Å, α=79.40±0.01°, β=85.19±0.01°, γ=86.55±0.01°, V=1277.1 Å$^3$, ρ=1.247Mgm$^{-3}$; at room temperature). Within the crystal structure, the molecules form intramolecular as well as intermolecular hydrogen bonds N—H . . . O=C. The intermolecular hydrogen bonds connect the molecules to chains parallel to the crystallographic a-axis.

Polymorph 4 may also be characterized by its DSC thermogram or its DVS (dynamic vapor sorption) water vapor sorption and desorption isotherms.

Polymorph 4 appears to be thermodynamically stable in a narrow temperature range around 90° C. Above and below that range, the other known polymorphs are more stable. Polymorph 4, however, can be obtained in a faster and thus easier crystallization process than polymorph 1, which is stable at room temperature. Thus, processes for the preparation of polymorph 4 are in particular suitable to purify raw compound I in a fast, easy to handle and convenient manner.

Moreover, the present invention relates to a chloroform solvate, a toluene solvate and a 1,2-dichlorobenzene solvate of 2'-{[2-(4-methoxy-phenyl)-acetylamino]-methyl}-biphenyl-2-carboxylic acid (2-pyridin-3-yl-ethyl)-amide.

The chloroform solvate according to the invention shows characteristic reflections in an X-ray powder diffractogram using CuK$_{α1}$ radiation in transmission mode at a 2θ angle [°] of 8.7±0.2(intensity: medium), 16.1±0.2(medium), 16.4±0.2 (medium), 17.1±0.2(strong), 19.9±0.2(medium), 20.4±0.2 (strong), 21.9±0.2(strong).

In one embodiment, the chloroform solvate may also be characterized by its X-ray powder diffraction pattern such as the one shown in FIG. 5 which has been obtained using CuK$_{α1}$ radiation in transmission mode, wherein the intensities of the reflections depicted in the Figure as well as those of the reflections specified above are not a prerequisite, but may vary, and represent another embodiment of the invention.

Outside the mother liquor, the chloroform solvate is only moderately stable and starts to transform to polymorph 2 Thus, a further aspect of the present invention relates to the use of the chloroform solvate of compound I for the production of polymorph 2, for example by subjecting it to conditions, such as an elevated temperature and/or reduced pressure, which facilitate the loss of chloroform.

The molar ratio of chloroform and compound I in the chloroform solvate can vary, depending on the details of the preparation such as the work-up procedure. In one embodiment of the invention the chloroform content is from about 1.1 to about 0.1, in another embodiment from about 1.1 to about 0.5, in another embodiment from about 1 to about 0.5, in another embodiment about 1, in another embodiment about 0.8 molar equivalents of chloroform, which latter chloroform content corresponds to the weight loss of samples of the chloroform solvate, which had been dried for a short time period, as determined by thermogravimetric analysis (TGA).

The toluene solvate according to the invention shows characteristic reflections in an X-ray powder diffractogram using CuK$_{α1}$ radiation in transmission mode at a 2θ angle [°] of 8.2±0.2(intensity: strong), 15.0±0.2(strong), 16.3±0.2(medium), 18.2±0.2 (medium), 21.3±0.2(medium), 21.6±0.2 (medium), 21.9±0.2(strong), 22.1±0.2 (medium), 22.5±0.2 (medium), 26.7±0.2(medium).

In one embodiment, the toluene solvate may also be characterized by its X-ray powder diffraction pattern such as the one shown in FIG. 6 which has been obtained using CuK$_{α1}$ radiation in transmission mode, wherein the intensities of the reflections depicted in the Figure as well as those of the reflections specified above are not a prerequisite, but may vary, and represent another embodiment of the invention.

According to temperature-resolved X-ray powder diffraction, DSC and TGA, the toluene solvate loses its solvent in the temperature range from about 80° C. to about 110° C. and transforms to polymorph 4 Thus, a further aspect of the present invention relates to the use of the toluene solvate for the production of polymorph 4.

The molar ratio of toluene and compound I in the toluene solvate can vary. In one embodiment of the invention the toluene content is from about 1.1 to about 0.1, in another embodiment from about 1.1 to about 0.3, in another embodiment from about 1 to about 0.3, in another embodiment from about 0.7 to about 0.3, in another embodiment about 0.5 molar equivalents of toluene which latter toluene content corresponds to the weight loss of samples of the toluene solvate as determined by TGA.

The 1,2-dichlorobenzene solvate according to the invention shows characteristic reflections in an X-ray powder diffractogram using CuK$_{α1}$ radiation in transmission mode at a 2θ angle [°] of 8.4±0.2(intensity: medium), 15.2±0.2(medium), 17.9±0.2(medium), 21.6±0.2(medium), 22.0±0.2 (strong), 26.4±0.2(medium).

In one embodiment, the 1,2-dichlorobenzene solvate may also be characterized by its X-ray powder diffraction pattern such as the one shown in FIG. 7 which has been obtained using CuK$_{α1}$ radiation in transmission mode, wherein the intensities of the reflections depicted in the Figure as well as those of the reflections specified above are not a prerequisite, but may vary, and represent another embodiment of the invention.

The 1,2-dichlorobenzene solvate can be used in the purification of compound I by recrystallizing it in the form of this solvate I. Thus, a further aspect of the present invention relates to the use of the 1,2-dichlorobenzene solvate of compound I for purifying compound I.

The molar ratio of 1,2-dichlorobenzene and compound I in the 1,2-dichlorobenzene solvate can vary. In one embodiment of the invention the 1,2-dichlorobenzene content is from about 1.1 to about 0.1, in another embodiment from about 1.1 to about 0.3, in another embodiment from about 1 to about 0.3, in another embodiment from about 0.7 to about 0.3, in another embodiment about 0.5 molar equivalents of 1,2-dichlorobenzene, which latter 1,2-dichlorobenzene content was determined in samples of the 1,2-dichlorobenzene solvate by $^1$H-NMR spectroscopy.

Another aspect of the present invention relates to the use of a polymorphic form or a mixture of polymorphic forms of 2'-{[2-(4-methoxy-phenyl)-acetylamino]-methyl}-biphenyl-2-carboxylic acid (2-pyridin-3-yl-ethyl)-amide according to the present invention, selected from polymorphic forms 1, 2, 3 and 4, as a pharmaceutical or medicament. One embodiment of the invention relates to the use of a polymorphic form selected from polymorphic forms 1, 2 and 3, or a mixture of polymorphic forms comprising at least one of polymorphic forms 1, 2 and 3, as a pharmaceutical or medicament. A further aspect of the present invention relates to a pharmaceutical composition comprising at least one polymorphic form of 2'-{[2-(4-methoxy-phenyl)-acetylamino]-methyl}-biphenyl-2-carboxylic acid (2-pyridin-3-yl-ethyl)-amide according to the present invention, selected from polymorphic forms 1, 2, 3 and 4, and one or more pharmaceutical acceptable excipients, i.e. inactive substances such as diluents and other auxiliaries. In one embodiment of the invention the pharmaceutical composition comprises at least one of polymorphic forms 1, 2 and 3 The pharmaceutical compositions, which can be employed when using compound I as a medicament in human medicine and veterinary medicine, normally contain a polymorph or polymorphs of compound I in a percentage from about 0.001% to about 90% by weight, in particular from about 0.001% to about 10% by weight, for example from about 0.05% to about 5% by weight, and an amount from about 0.2 mg to about 1000 mg, in particular from about 1 mg to about 750 mg, per unit dose, but depending on the kind of the pharmaceutical composition and other particulars of the specific case, the percentage and amount may deviate from the indicated ones.

In general, suitable excipients are known to the person skilled in the art. A diluent, or carrier substance, is any compound which is pharmaceutical acceptable and suitable to increase the bulk volume of the pharmaceutical composition, so that the final product has the proper form and volume for administration and dosage by the patient or physician. Examples of diluents are water, vegetable fats and oils, lactose, sucrose, glucose, mannitol, sorbitol, calcium carbonate, calcium phosphate, kaolin, microcrystalline cellulose, starch etc. and combinations thereof. Examples of other auxiliaries, which may be present in a pharmaceutical composition for attaining the desired property profile and/or supporting its manufacture, are antiadherents, binders (e.g. acaia gum, gelatin, cellulose, cellulose derivatives, polyvinylpyrrolidone, sodium alginate, starch, sucrose, polyethylene glycol, etc.), buffer salts, coatings (e.g. cellulose, synthetic polymers, shellac, polysachamides etc.), disintegrants (e.g. starch, cellulose, crosslinked polyvinylpyrrolidone, sodium starch glycolate, sodium carboxymethyl cellulose, methyl cellulose, gums such as agar, guar, etc.), flavors and colors, glidants, lubricants (e.g. talc, silica, magnesium stearate etc.), preservatives (e.g. antioxidants like vitamin A, vitamin E, vitamin C, retinyl palmitate and selenium, methionine, cysteine, citric acid, sodium citrate, methylparaben, propylparaben etc.), sorbents, sweeteners, wetting agents and others including e.g. gelatin, casein, lecithin, gum acacia, cholesterol, tragacanth, stearic acid, benzalkonium chloride, calcium stearate, glycerol monostearate, cetostearyl alcohol, sorbitan esters, polyoxyethylene alkyl ethers, polyoxyethylene castor oil derivatives, polyoxyethylene sorbitan fatty acid esters, polyethylene glycols, polyoxyethylene stearates, colloidal silicon dioxide, phosphates, sodium dodecylsulfate, carboxymethylcellulose calcium, cellulose derivatives, magnesium aluminum silicate, triethanolamine, polyvinyl alcohol, polyvinylpyrrolidone etc., as well as any combination thereof.

The pharmaceutical compositions according to the invention may have any form suitable for dosage and administration in the desired use of compound I and, e.g., be a liquid, syrup, elixir, injectable solution, suspension, ointment, powder, tablet, pill, hard or soft capsule, lozenge, and the like. The pharmaceutical compositions can be administered, for example, orally, bucally, rectally, parenterally, intravenously, subcutaneously, nasally, topically, by inhalation or by ophthalmic or transdermal routes, especially orally, intravenously or nasally, the preferred administration depending on the particular case. The dosage, which is employed when treating a subject, preferably a mammal, more preferably a human, with compound I in the form of one or more polymorphs according to the invention and which is effective for obtaining the desired therapeutic result, varies and is determined by the physician in view of the particulars of the specific case. As is known in the art, the dosage depends on a variety of factors such as, for example, the severity of the condition being treated, general health, the route of administration, body weight, gender, diet, time and route of administration, the desired duration of treatment, rates of absorption and excretion, combination with other drugs, and others. The total daily dose of a polymorph or polymorphs of compound I according to the invention may be administered to a patient in a single dose or divided doses.

In one embodiment of the present invention, a polymorph or polymorphs of compound I according to the invention, or a pharmaceutical composition comprising them, is used in the treatment, including therapy, of atrial arrhythmia, for example atrial fibrillations or atrial flutter, and/or sleep-related respiratory disorders, for example sleep-related respiratory disorders selected from the group consisting of sleep apnea, for example central sleep apnea or obstructive sleep apnea, Cheyne-Stokes respiration, snoring, disrupted central respiratory drive, upper airway resistance syndrome and sudden child death, especially obstructive sleep apnea. Other respiratory disorders like postoperative hypoxia, apnea, muscle-related respiratory disorders, respiratory disorders after long-term ventilation, respiratory disorders during adaptation in high mountains, acute and chronic lung disorders with hypoxia and hypercapnia, may also be treated with a polymorph of polymorphs of compound I according to the invention or a pharmaceutical composition comprising them.

Obstructive sleep apnea arises through the reduced inspiratory pressure which is generated by the diaphragm and chest muscles in the course of inhalation into the upper respiratory pathways in the presence of contraction of the upper respiratory pathways. Constricted anatomic conditions of the upper respiratory pathways are present in the case of obesity (lipotrophy) and anatomic predisposition, e.g. retrognathia. In persons having this predisposition, the tone of the dilating muscle structure of the upper respiratory pathway muscle structure must always be increased in comparison to healthy persons in order to prevent collapse. The genioglossus muscle, a muscle at the base of the tongue which is innervated by the hypoglossal nerve, is the most important of the dilating muscles of the upper respiratory pathways. While the muscle tone in the upper respiratory pathways is still sufficiently high in the wakeful state to prevent respiratory disorders, it falls greatly in sleep, such that it is too low in relation to the reduced inspiratory pressure. This disparity leads to the collapse of the upper respiratory pathways (obstructive apnea) during the inhalation. In the case of high constriction of the upper respiratory pathways and correspondingly high tissue pressure, a collapse can occur even during exhalation, i.e. without reduced pressure. An increase in the muscle tone of the upper respiratory pathways through compound I can prevent obstructive apneas.

Snoring is generated by flow-related vibrations in the upper respiratory pathways. It arises in the case of excessively narrow upper respiratory pathways with simultaneously insufficient muscle tone of the upper respiratory pathways and hence has a close pathophysiological relationship to obstructive sleep apnea. Snoring can thus be regarded to some extent as a precursor of obstructive sleep apnea. An increase in the muscle tone of the upper respiratory pathways through compound I therefore can prevent both snoring and obstructive sleep apnea. Central apneas are caused by central disruptions of respiratory regulation. They can be prevented by the simultaneous respiration-stimulating action of compound I.

Accordingly, a further aspect of the present invention relates to the use of a polymorphic form or a mixture of polymorphic forms of 2'-{ [2-(4-methoxy-phenyl)-acetylamino]-methyl}-biphenyl-2-carboxylic acid (2-pyridin-3-yl-ethyl)-amide according to the invention for the manufacture of a medicament for the treatment, including therapy, of sleep-related respiratory disorders or atrial arrhythmia. In a particular preferred embodiment the sleep-related respiratory disorder is sleep apnea, preferably obstructive sleep apnea.

In one embodiment of the invention, the pharmaceutical composition according to the invention comprises at least one further active agent, in particular an active agent for the treatment, including therapy, of atrial arrhythmia and/or sleep-related respiratory disorders.

According to one embodiment of the invention, the pharmaceutical composition according to the invention contains polymorph 1 of compound I. According to another embodiment, it contains polymorph 1 of compound I in combination with polymorph 2 of compound I and/or polymorph 3 of compound I and/or polymorph 4 of compound I, for example polymorph 1 of compound I in combination with polymorph 3 of compound I or polymorph 1 of compound I in combination with polymorph 4 of compound I. According to another embodiment of the invention, the pharmaceutical composition according to the invention contains polymorph 3 of compound I. According to another embodiment, it contains polymorph 3 of compound I in combination with polymorph 1 of compound I and/or polymorph 2 of compound I and/or polymorph 4 of compound I, for example polymorph 3 of compound I in combination with polymorph 4.

Another aspect of the present invention relates to processes for the preparation of the polymorphic forms and solvates according to the invention. In a further aspect, the present invention relates to a process for the purification of 2'-{[2-(4-methoxy-phenyl)-acetylamino]-methyl}-biphenyl-2-carboxylic acid (2-pyridin-3-yl-ethyl)-amide comprising a crystallization step, wherein polymorph 1, polymorph 2, polymorph 3, polymorph 4, the chloroform solvate, the toluene solvate or the 1,2-dichlorobenzene solvate of 2'-{[2-(4-methoxy-phenyl)-acetylamino]-methyl}-biphenyl-2-carboxylic acid (2-pyridin-3-yl-ethyl)-amide described above is obtained. Said process comprises preferably the preparation of polymorph 1, polymorph 2, polymorph 3, polymorph 4, chloroform solvate, toluene solvate or 1,2-dichlorobenzene solvate as outlined below.

In general, the polymorphic forms and solvates of the invention can be obtained by crystallizing or recrystallizing compound I, starting from a solution of compound I or from a suspension of compound I or from solid compound I. A solution of compound I, or a suspension of compound I, may have been obtained at the end of the chemical synthesis of compound I, or it may have been obtained by dissolving or suspending previously synthesized crude compound I. The term "crude compound I" comprises any form of compound I, e.g. the material directly obtained from chemical synthesis, a distinct polymorphic form or solvate or a mixture of polymorphic forms and/or solvates, which may not have been characterized with respect to its crystal properties, and which is to be transformed to a distinct polymorphic form or solvate or to another distinct polymorphic form or solvate. More specifically, the polymorphic forms and solvates of the invention can be obtained by (a) providing a solution or suspension of compound I, for example by dissolving or suspending crude compound I in a suitable solvent, wherein a solution of compound I generally is a clear solution and may optionally have been filtered, (b) maintaining, heating, cooling and/or concentrating the solution or suspension and/or adding one or more further solvents, with or without agitation such as stirring, to form a precipitate of crystals of a desired distinct polymorph or solvate or to allow the formation of a desired distinct polymorph or solvate, and (c) isolating the distinct polymorph or solvate.

The processes for preparing polymorphic forms and solvates of compound I can be performed with conventional equipment and according to standard procedures. For example, concentrating of a solution or suspension in step (b) may be done by distilling off solvent partially or totally at atmospheric pressure or at reduced pressure. Isolating of a polymorph or solvate in step (c) may be done by any conventional technique such as filtration or vacuum filtration or centrifugation. Isolating may also comprise drying, e.g. by applying elevated temperatures and/or reduced pressure, for example at moderately reduced pressure at about room temperature, i.e. a temperature of about 18° C. to about 25° C., for example about 20° C., or at about 40° C.

In a preferred embodiment, the solution or suspension may be seeded in step (a) or step (b) to promote crystallization or polymorph transformation. Seeding is preferably done with a small amount of the desired polymorph or solvate, for example polymorph 1 or polymorph 2 or polymorph 3 or polymorph 4.

One aspect of the present invention relates to a process for the preparation of polymorph 1 of 2'-{[2-(4-methoxy-phenyl)-acetylamino]-methyl}-biphenyl-2-carboxylic acid (2-pyridin-3-yl-ethyl)-amide, the process comprising the steps of (a) suspending 2'-{[2-(4-methoxy-phenyl)-acetylamino]-methyl}-biphenyl-2-carboxylic acid (2-pyridin-3-yl-ethyl)-amide at about room temperature in a solvent selected from the group consisting of methanol, ethanol, methanol/water, ethanol/water, methyl acetate, ethyl acetate, butyl acetate, methyl ethyl ketone, tetrahydrofuran, 1,4-dioxane, acetonitrile and methylene chloride to obtain a suspension;

(b) maintaining the suspension at about room temperature for a time period sufficient to allow formation of polymorph 1 crystals, for example for about 1 day to about 50 days, such as for about 28 days;

(c) isolating the precipitate of polymorph 1;

or (a') suspending 2'-{[2-(4-methoxy-phenyl)-acetylamino]-methyl}-biphenyl-2-carboxylic acid (2-pyridin-3-yl-ethyl)-amide at about room temperature in a solvent selected from the group consisting of ethanol and isopropanol to obtain a suspension;

(b') maintaining the suspension at a temperature of about 0° C. to about 45° C., preferably about 15° C. to about 25° C., more preferably at about 20° C., for a time period sufficient to allow formation of polymorph 1 crystals, for example for about 1 day to about 50 days, such as for about 28 days;

(c') isolating the precipitate of polymorph 1;

or (a") suspending 2'-{[2-(4-methoxy-phenyl)-acetylamino]-methyl}-biphenyl-2-carboxylic acid (2-pyridin-3-yl-ethyl)-amide at about room temperature in acetone to obtain a suspension;

(b") maintaining the suspension at a temperature of about 15° C. to about 40° C. for a time period sufficient to allow formation of polymorph 1 crystals, for example for about 1 day to about 50 days, such as for about 28 days;

(c") isolating the precipitate of polymorph 1;

or (a'") dissolving 2'-{[2-(4-methoxy-phenyl)-acetylamino]-methyl}-biphenyl-2-carboxylic acid (2-pyridin-3-ylethyl)-amide in ethanol to obtain a solution, preferably with heating to a temperature of about 60° C. to about 70° C.;

(b''') rapid cooling of the solution to a temperature of about 0° C., preferably with stirring;

(c''') isolating the precipitate of polymorph 1.

According to a preferred embodiment, the suspension may be seeded with polymorph 1 crystals, preferably during step (b), (b'), (b'') or (b''').

A further aspect of the present invention relates to a process for the preparation of polymorph 2 of 2'-{[2-(4-methoxy-phenyl)-acetylamino]-methyl}-biphenyl-2-carboxylic acid (2-pyridin-3-yl-ethyl)-amide, the process comprising the steps of (a) suspending 2'-{[2-(4-methoxy-phenyl)-acetylamino]-methyl}-biphenyl-2-carboxylic acid (2-pyridin-3-yl-ethyl)-amide at about room temperature in chloroform to obtain a suspension;

(b) maintaining the suspension at about room temperature for a time period sufficient to allow formation of a precipitate of chloroform solvate of compound I, for example for about 1 day to about 50 days, such as for about 28 days;

(c) isolating the precipitate;

(d) maintaining the precipitate at a temperature of about 20° C. to about 100° C., preferably at about room temperature or at a temperature of about 60° C. to about 100° C., for a time period sufficient to allow formation of polymorph 2, for example for about 1 day to 50 days, such as for about 28 days if the temperature is room temperature;

(e) isolating polymorph 2;

or (a') dissolving 2'-{[2-(4-methoxy-phenyl)-acetylamino]-methyl}-biphenyl-2-carboxylic acid (2-pyridin-3-yl-ethyl)-amide in chloroform to obtain a solution, preferably with heating to a temperature of about 60° C.;

(b') rapid cooling of the solution to a temperature of about 0° C. for a time period sufficient to allow formation of a precipitate of chloroform solvate of compound I, for example for about 1 hour, preferably with stirring;

(c') isolating the precipitate;

(d') maintaining the precipitate at a temperature of about 20° C. to about 100° C., preferably at about room temperature or at a temperature of about 60° C. to about 100° C., for a time period sufficient to allow formation of polymorph 2, for example for about 1 day to 50 days, such as for about 28 days if the temperature is room temperature;

(e') isolating polymorph 2.

According to a preferred embodiment, the suspension or solution may be seeded with chloroform solvate of compound I, preferably during step (b) or (b').

A further aspect of the present invention relates to a process for the preparation of polymorph 3 of 2'-{[2-(4-methoxy-phenyl)-acetylamino]-methyl}-biphenyl-2-carboxylic acid (2-pyridin-3-yl-ethyl)-amide, the process comprising the steps of (a) dissolving 2'-{[2-(4-methoxy-phenyl)-acetylamino]-methyl}-biphenyl-2-carboxylic acid (2-pyridin-3-yl-ethyl)-amide in butyl acetate to obtain a solution, for example at about room temperature or at a temperature of about 55° C. to about 65° C.;

(b) concentrating the solution by evaporating butyl acetate at an elevated temperature, for example at about 55° C. to about 65° C., and a reduced pressure, for example at a pressure from about 200 mbar to about 20 mbar, and/or cooling, for example to a temperature of about 0° C., for a time period sufficient to allow formation of a precipitate of polymorph 3 crystals, for example for about 1 hour to about 4 hours;

(c) isolating polymorph 3.

Depending on the crystallization conditions, in this process polymorph 3 may be obtained together with another polymorph, for example polymorph 1 or 4. According to a preferred embodiment, the solution may be seeded with polymorph 3 crystals, preferably during step (b).

A further aspect of the present invention relates to a process for the preparation of polymorph 4 of 2'-{[2-(4-methoxy-phenyl)-acetylamino]-methyl}-biphenyl-2-carboxylic acid (2-pyridin-3-yl-ethyl)-amide, the process comprising the steps of (a) dissolving 2'-{[2-(4-methoxy-phenyl)-acetylamino]-methyl}-biphenyl-2-carboxylic acid (2-pyridin-3-yl-ethyl)-amide in a solvent selected from the group consisting of acetone, butyl acetate and acetonitrile at a temperature of about 55° C. to about 70° C., preferably about 55° C. to about 60° C., more preferably at about 56° C. for acetone, preferably about 60° C. to about 70° C., more preferably at about 65° C. for butyl acetate or acetonitrile, to obtain a solution;

(b) rapid cooling, for example over about 10 minutes or over about 30 minutes depending on the batch size, of the solution to a temperature of about −5° C. to about 5° C., and maintaining it at this temperature, for example at about 0° C., for a time period sufficient to allow formation of a precipitate of polymorph 4 crystals, for example for about 1 hour with stirring;

(c) isolating the precipitate of polymorph 4;

or (a') dissolving 2'-{[2-(4-methoxy-phenyl)-acetylamino]-methyl}-biphenyl-2-carboxylic acid (2-pyridin-3-yl-ethyl)-amide in a solvent selected from the group consisting of water/methanol, ethanol, acetone and acetonitrile at a temperature of about 55° C. to about 70° C., preferably at about 65° C. in the case of water/methanol, ethanol and acetonitrile, to obtain a solution;

(b') concentrating the solution by evaporating solvent partially or totally at a temperature of about 55° C. to about 70° C., preferably at about 65° C. in the case of water/methanol, ethanol and acetonitrile, and/or slow cooling to a temperature of about 5° C. to about 15° C., preferably to about 10° C., for a time period sufficient to allow formation of a precipitate of polymorph 4 crystals, for example about 10 hours to 30 hours, such as about 20 hours;

(c') isolating the precipitate of polymorph 4;

or (a'') dissolving 2'-{[2-(4-methoxy-phenyl)-acetylamino]-methyl}-biphenyl-2-carboxylic acid (2-pyridin-3-yl-ethyl)-amide in methanol to obtain a solution;

(b'') adding diisopropyl ether to the solution to form a precipitate of polymorph 4 crystals, for example at about room temperature with stirring;

(c'') isolating the precipitate of polymorph 4.

According to a preferred embodiment, the solution may be seeded with polymorph 4 crystals, preferably during step (b), (b') or (b'').

Alternatively, polymorph 4 can be prepared as described in WO 01/25189, U.S. Pat. No. 6,531,495, US 2007/0043091 and WO 2007/124849.

A further aspect of the present invention relates to a process for the preparation of chloroform solvate of 2'-{[2-(4-methoxy-phenyl)-acetylamino]-methyl}-biphenyl-2-carboxylic acid (2-pyridin-3-yl-ethyl)-amide, the process comprising the steps of (a) suspending 2'-{[2-(4-methoxy-phenyl)-acetylamino]-methyl}-biphenyl-2-carboxylic acid (2-pyridin-3-yl-ethyl)-amide at about room temperature in chloroform to obtain a suspension;
(b) maintaining the suspension at about room temperature for a time period sufficient to form a precipitate of chloroform solvate, for example for about 1day to about 50 days, such as for about 28days;
(c) isolating the precipitate of chloroform solvate;
or
(a') dissolving 2'-{[2-(4-methoxy-phenyl)-acetylamino]-methyl}-biphenyl-2-carboxylic acid (2-pyridin-3-yl-ethyl)-amide in chloroform to obtain a solution, preferably with heating to a temperature of about 60° C.;
(b') rapid cooling of the solution to about 0° C. for a time period sufficient to form a precipitate of chloroform solvate, for example for about 1hour, preferably with stirring;
(c') isolating the precipitate of chloroform solvate.

According to a preferred embodiment, the suspension or solution may be seeded with chloroform solvate of compound I, preferably during step (b) or (b').

A further aspect of the present invention relates to a process for the preparation of 1,2-dichlorobenzene solvate of 2'-{[2-(4-methoxy-phenyl)-acetylamino]-methyl}-biphenyl-2-carboxylic acid (2-pyridin-3-yl-ethyl)-amide, the process comprising the steps of
(a) suspending 2'-{[2-(4-methoxy-phenyl)-acetylamino]-methyl}-biphenyl-2-carboxylic acid (2-pyridin-3-yl-ethyl)-amide at about room temperature in 1,2-dichlorobenzene to obtain a suspension;
(b) maintaining the suspension at about room temperature for a time period sufficient to allow formation of 1,2-dichlorobenzene solvate, for example for about 1day to about 50days, such as for about 28days;
(c) isolating the precipitate of 1,2-dichlorobenzene solvate.

According to a preferred embodiment, the suspension may be seeded with 1,2-dichlorobenzene solvate of compound I, preferably during step (b).

A further aspect of the present invention relates to a process for the preparation of toluene solvate of 2'-{[2-(4-methoxy-phenyl)-acetylamino]-methyl}-biphenyl-2-carboxylic acid (2-pyridin-3-yl-ethyl)-amide, the process comprising the steps of
(a) suspending 2'-{[2-(4-methoxy-phenyl)-acetylamino]-methyl}-biphenyl-2-carboxylic acid (2-pyridin-3-yl-ethyl)-amide at about room temperature in toluene to obtain a suspension;
(b) maintaining the suspension at about room temperature for a time period sufficient to allow formation of toluene solvate, for example for about 1day to about 50days, such as for about 28days;
(c) isolating the precipitate of toluene solvate.

According to a preferred embodiment, the suspension may be seeded with toluene solvate of compound I, preferably during step (b).

DESCRIPTION OF THE FIGURES

FIG. 19—FT Raman spectrum of polymorph 4of compound I in the wave number range from 1700to 200cm$^{-1}$(x-axis: wave number [cm$^{-1}$]; y-axis: intensity [arbitrary units]).

EXAMPLES

Figure 1:
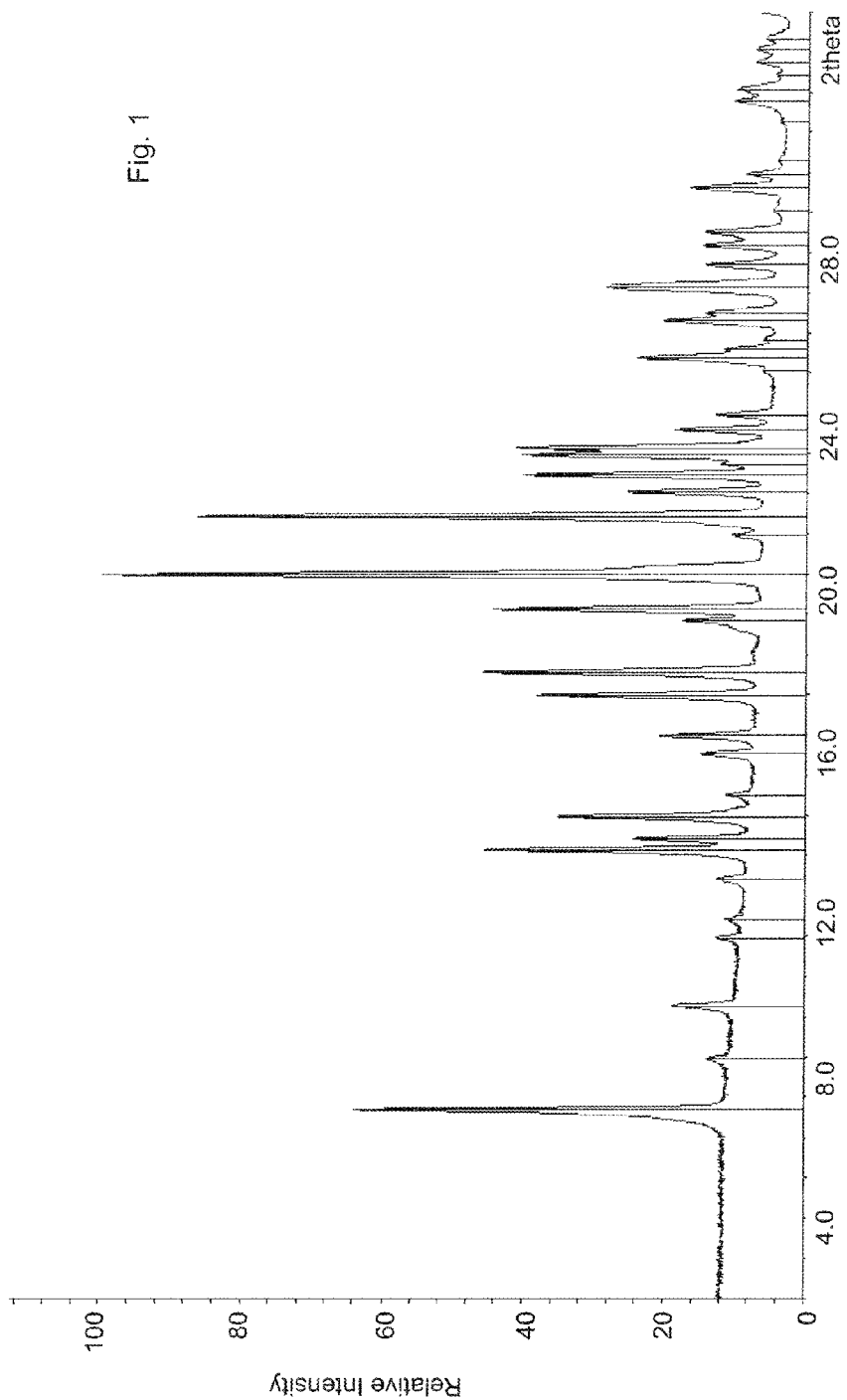
FIG. 1—X-ray powder diffraction pattern of polymorph 1of compound I, measured in transmission mode with $CuK_{\alpha 1}$ radiation at room temperature (x-axis: diffraction angle 2theta (2θ) [°]; y-axis: relative intensity [% of the highest reflection])
FIG. 2—X-ray powder diffraction pattern of polymorph 2of compound I, measured in transmission mode with $CuK_{\alpha 1}$ radiation at room temperature (x-axis: diffraction angle 2theta (2θ) [°]; y-axis: relative intensity [% of the highest reflection])
FIG. 3—X-ray powder diffraction pattern of polymorph 3of compound I, measured in transmission mode with $CuK_{\alpha 1}$ radiation at room temperature (x-axis: diffraction angle 2theta (2θ) [°]; y-axis: relative intensity [% of the highest reflection])
FIG. 4—X-ray powder diffraction pattern of polymorph 4of compound I, measured in transmission mode at room temperature with $CuK_{\alpha 1}$ radiation (x-axis: diffraction angle 2theta (2θ) [°]; y-axis: relative intensity [% of the highest reflection])
FIG. 5—X-ray powder diffraction pattern of chloroform solvate of compound I, measured in transmission mode with $CuK_{\alpha 1}$ radiation at room temperature (x-axis: diffraction angle 2theta (2θ) [°]; y-axis: relative intensity [% of the highest reflection])
FIG. 6—X-ray powder diffraction pattern of toluene solvate of compound I, measured in transmission mode with $CuK_{\alpha 1}$ radiation at room temperature (x-axis: diffraction angle 2theta (2θ) [°]; y-axis: relative intensity [% of the highest reflection])
FIG. 7—X-ray powder diffraction pattern of 1,2-dichlorobenzene solvate of compound I, measured in transmission mode with $CuK_{\alpha 1}$ radiation at room temperature (x-axis: diffraction angle 2theta (2θ) [°]; y-axis: relative intensity [% of the highest reflection])
FIG. 8—FT Raman spectrum of polymorph 1of compound I in the wave number range from 3500to 200cm$^{-1}$(x-axis: wave number [cm$^{-1}$]; y-axis: intensity [arbitrary units]).

2'-{[2-(4-Methoxy-phenyl)-acetylamino]-methyl}-biphenyl-2-carboxylic acid (2-pyridin-3-yl-ethyl)-amide is abbreviated as "compound I".

Formation of the Polymorphs and Solvates According to the Invention

The following examples illustrate the formation of the polymorphs and solvates of the present invention by way of example. Methods for the preparation of crude compound I as the starting material are known to the person skilled in art from WO 01/25189, U.S. Pat. No. 6,531,495 and WO 2007/124849, for example. Drying at reduced pressure was carried out at a pressure of about 0.2 bar.

Formation of polymorph 1

(a) 1.003g of compound I were dissolved in 1.86ml of ethanol at 65° C. The temperature of the solution was reduced fast to 0° C. with continuous stirring. After about 1hour of stirring, the precipitate was isolated via vacuum filtration and dried overnight at reduced pressure at room temperature.

(b) 45g of compound I (polymorph 4) were suspended in 35ml of ethanol, seeded with a small amount of polymorph 1 and stirred overnight at room temperature. The solid was isolated via vacuum filtration the next day and dried at reduced pressure at room temperature. Yield: 40g of pure polymorph 1.

(c) 0.213g of compound I (polymorph 4) were suspended in 0.6ml of isopropanol, seeded with a small amount of polymorph 1 and stirred for 4weeks in a closed vessel at room temperature. The solid was isolated via vacuum filtration and dried at reduced pressure at room temperature.

Formation of Polymorph 2

(a) 1.003g of compound I were dissolved in 0.94ml of chloroform at the boiling temperature. The temperature of the solution was reduced fast to 0° C. with continuous stirring. The precipitate was isolated via vacuum filtration and dried overnight at reduced pressure at room temperature.

(b) 0.202g of compound I (polymorph 4) were suspended in 0.5ml of chloroform and stirred for 4weeks in a closed vessel at room temperature. The solid was isolated via vacuum filtration and dried at reduced pressure at room temperature.

Formation of Polymorph 3

404.2g of a yellowish solution of crude compound I obtained from the last synthesis step was concentrated in a rotary evaporator at a temperature of 60° C. and a pressure of 145 to 40mbar to give 122.4g of a yellowish suspension. Compound I crystallized during concentration. The suspension, which was easy to stir, was stirred at room temperature for 30minutes and then cooled to a temperature of 0° C. to 2° C. and stirred for another 2.5hours. Compound I was filtered off with suction, washed twice with butyl acetate having a temperature of 5° C. on the suction filter, and dried for 20hours in a vacuum cabinet drier at 40° C. with nitrogen overlaying. 21.2g of a white, voluminous finely crystalline solid were obtained which consisted predominantly of polymorph 3 with parts of polymorph 4.

Formation of Polymorph 4

(a) 0.207g of compound I were dissolved in 0.4ml of ethanol at 65° C., and the solvent was evaporated from the open vessel at 65° C. with continuous stirring.

(b) 0.218g of compound I were dissolved in 6.3ml of butyl acetate at 65° C. Subsequently, the vessel bearing the solution was brought to an environment having 0° C., with the solution being continuously stirred. After 1hour, the precipitate was isolated via vacuum filtration and dried overnight at reduced pressure at room temperature.

(c) 0.223g of compound I were dissolved in 0.5ml of acetone at about 56° C. The temperature of the solution was reduced slowly to 10° C. within 20hours with continuous stirring. The precipitate was isolated via vacuum filtration and dried overnight at reduced pressure at room temperature.

(d) 0.231g of compound I were dissolved in 0.4ml of acetonitrile at about 65° C. The vessel bearing the solution was brought fast to an environment having 0° C. The solution was stirred for about 1hour until crystallization took place. The precipitate was isolated via vacuum filtration and dried overnight at reduced pressure at room temperature.

(e) 0.213g of compound I were dissolved in 0.5ml of acetone at about 56° C. The vessel bearing the solution was brought fast to an environment having 0° C. The solution was stirred for about 1hour until crystallization took place. The precipitate was isolated via vacuum filtration and dried overnight at reduced pressure at room temperature.

(f) 0.215g of compound I were dissolved in 0.4ml of acetonitrile at about 65° C. The temperature of the solution was reduced to 10° C. within 20hours with continuous stirring. The precipitate was isolated via vacuum filtration and dried overnight at reduced pressure at room temperature.

Formation of 1,2-dichlorobenzene solvate 0.220g of compound I (polymorph 4) were suspended in 0.6ml of 1,2-dichlorobenzene. The solution was stirred in a closed vessel at room temperature for four weeks. The solid present in the suspension was isolated via vacuum filtration and dried at reduced pressure at room temperature.

Formation of Chloroform Solvate (a) 1.003g of compound I (polymorph 4) were dissolved in 0.94ml of chloroform at the boiling temperature and cooled down fast to 0° C. with continuous stirring. The precipitate present in the suspension after crystallization consisted of the chloroform solvate.

(b) 0.202g of compound I (polymorph 4) were suspended in 0.5ml of chloroform. The suspension was stirred at room temperature for 4weeks. The solid present in the suspension consisted of the chloroform solvate.

Formation of Toluene Solvate 0.206g of compound I (polymorph 4) were suspended in 1.20ml of toluene. The suspension was stirred at room temperature for 4weeks. The solid present in the suspension was isolated via vacuum filtration and dried overnight at reduced pressure at room temperature.

Analytical Methods and Operation Conditions

X-Ray Powder Diffraction (XRPD)

Figure 2:
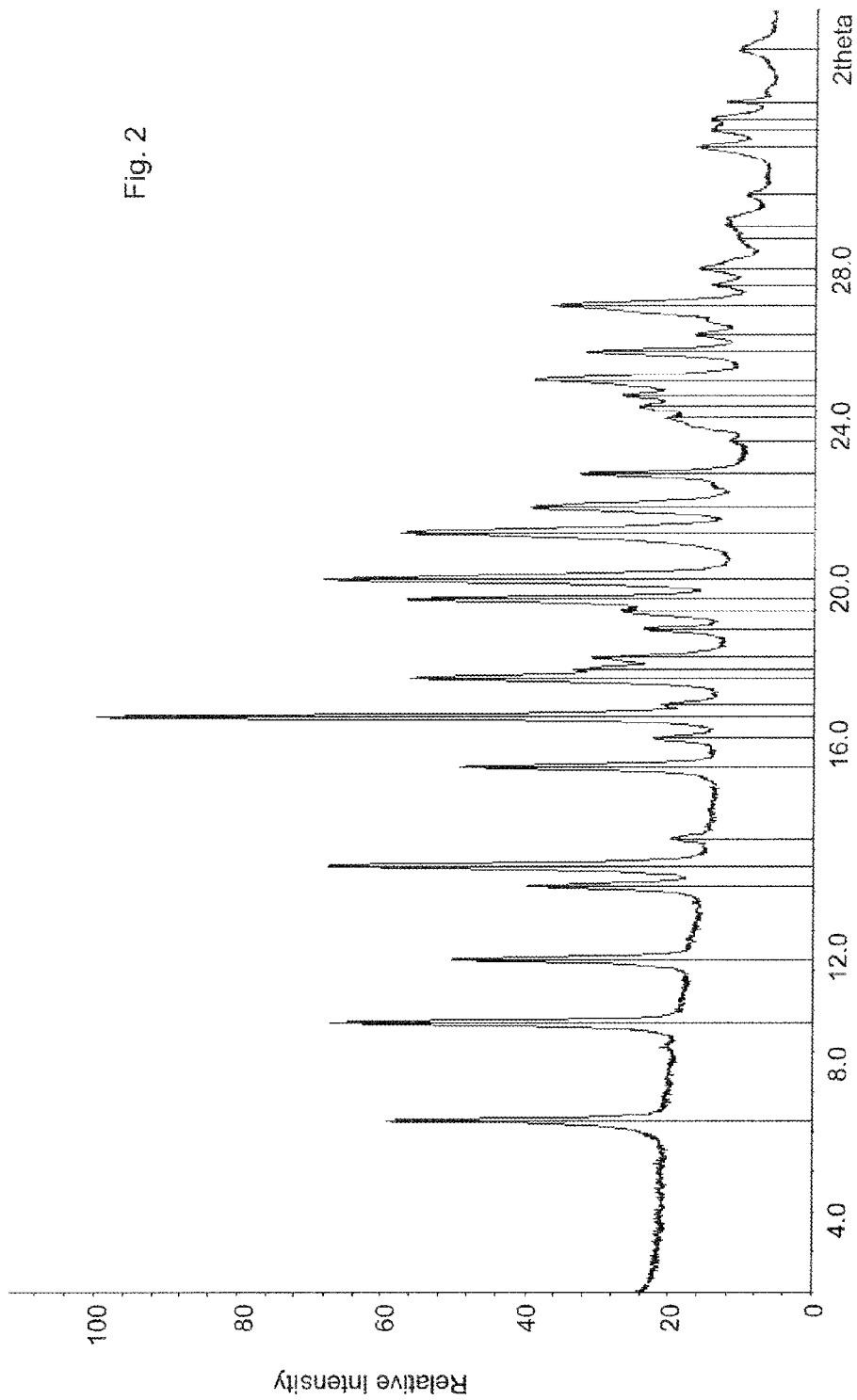
Figure 3:
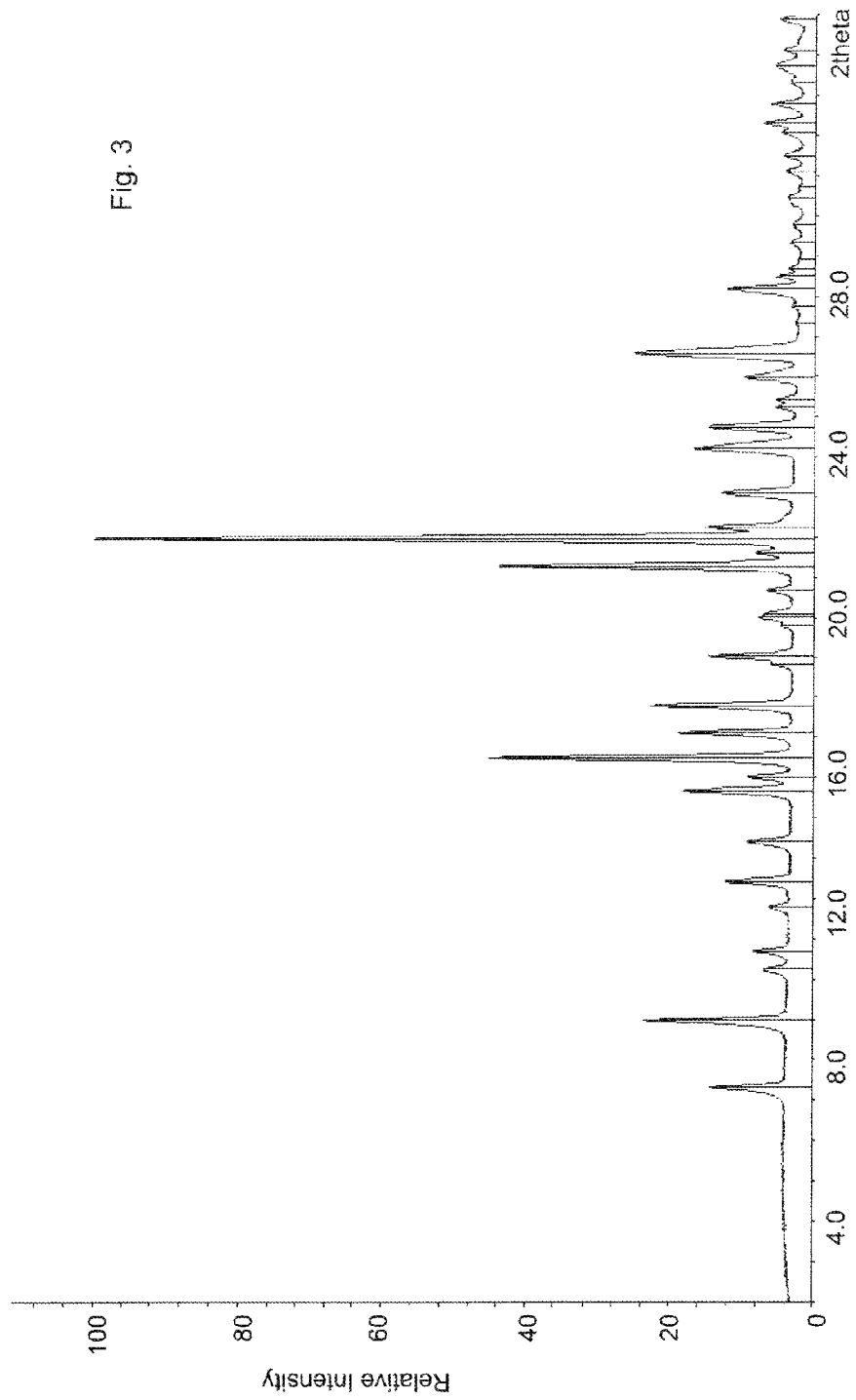
Figure 4:
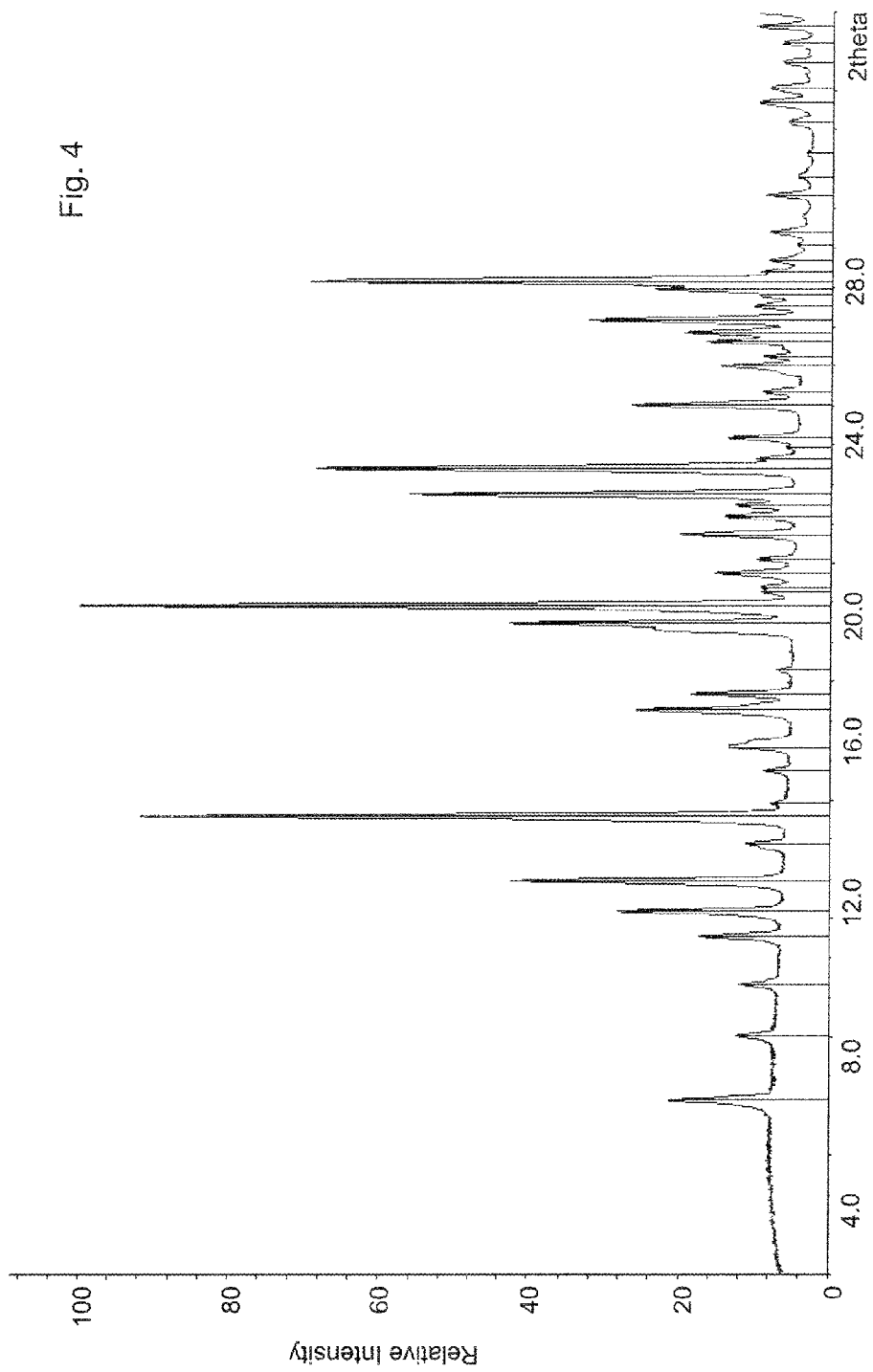
Figure 5:
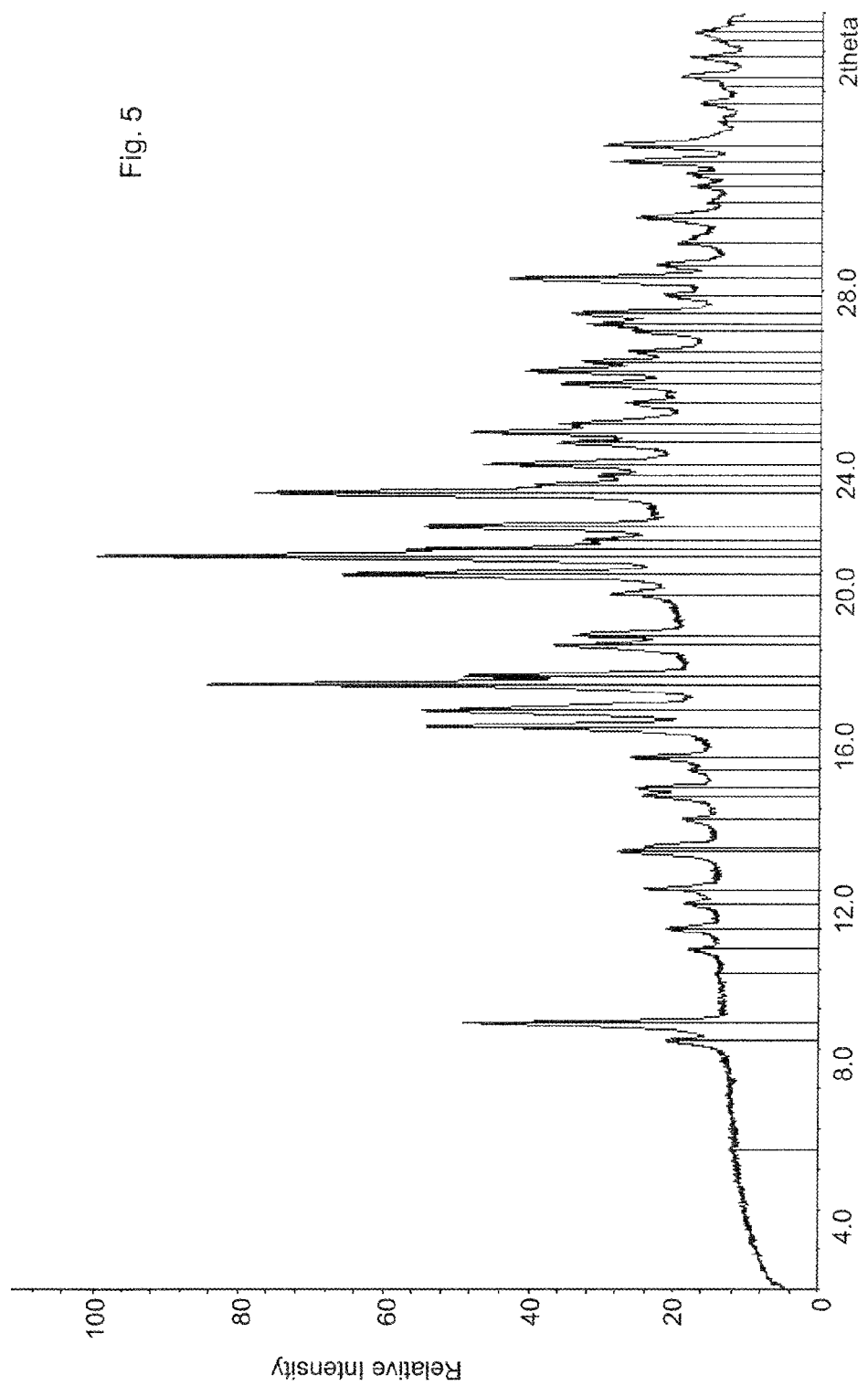
Figure 6:
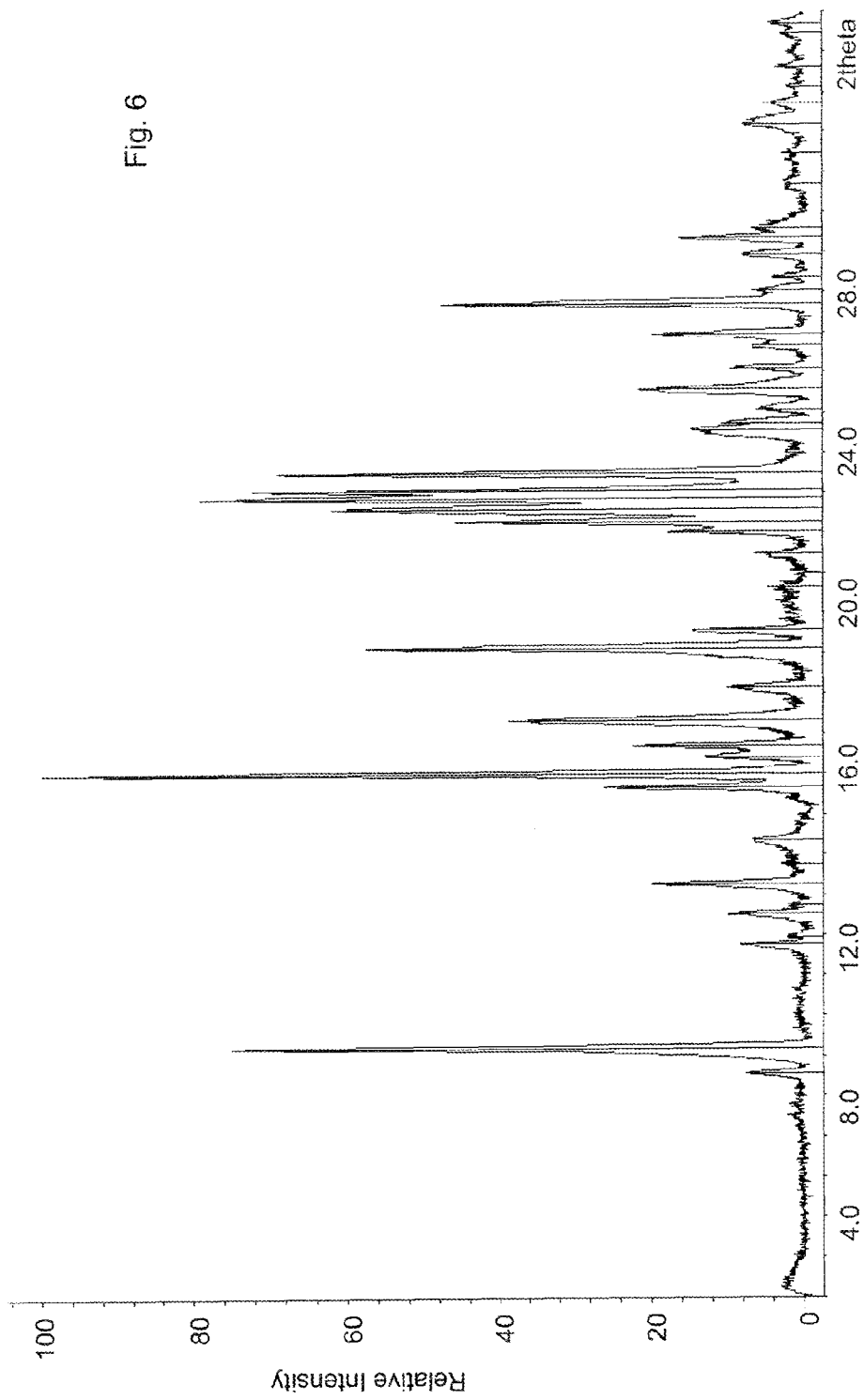
Figure 7:
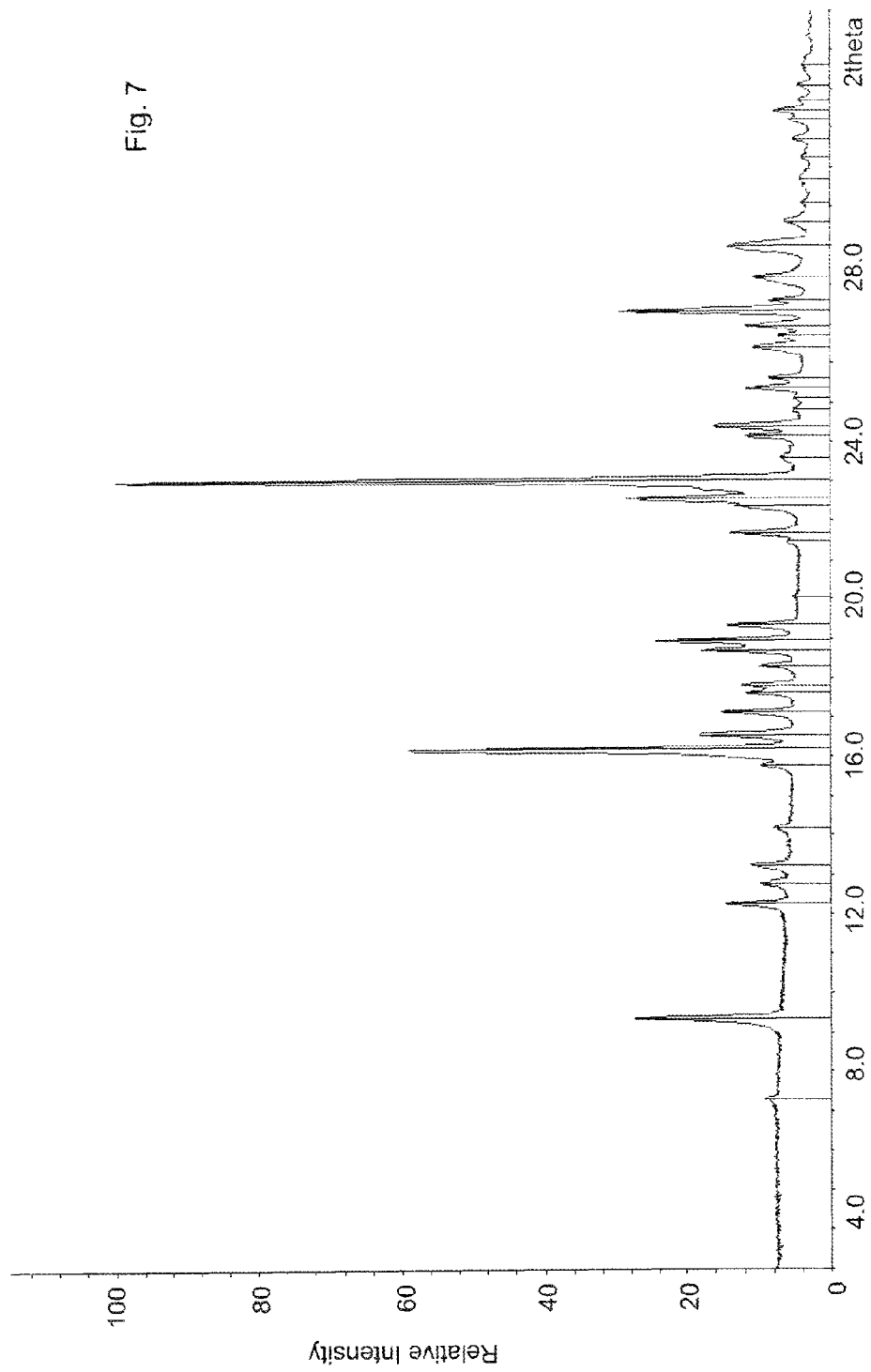

All X-ray powder diffraction was performed with Stoe Stadi-P transmission diffractometers using $CuK_{\alpha 1}$ radiation. For room temperature powder diffraction, linear position sensitive detectors were used, while for temperature-resolved XRPD image plate position sensitive detectors (IP-PSDs) were used. Unless stated otherwise, X-ray powder diffraction was performed at room temperature. Dry samples were investigated in a flat preparation whereas suspensions were investigated in quartz glass capillaries. The measured data were evaluated and plotted with the Software WinXPOW V1.1 The observed X-ray powder diffractograms of phases 1, 2, 3 and 4 as well as chloroform solvate, toluene solvate and 1,2-dichlorobenzene solvate of compound I are displayed in FIGS. 1 to 7. The 2θ (2theta) angles in ° (degree) and the relative intensities of characteristic reflections are specified above, wherein the relative intensity of a reflection is designated as "strong" if it is more than 75% of the intensity of the most intense reflection or it is the most intense reflection itself, and as "medium" if it is between 20% and 75% of the intensity of the most intense reflection.

Temperature-resolved X-ray powder diffractograms showed that phases 1, 2, 3 and 4 of compound I melted without preceding solid-solid transitions.

Differential Scanning Calorimetry (DSC)

All DSC measurements were performed with a Mettler DSC822e (module DSC822e/700/109/414935/0025). If not indicated differently, 40μl Al crucibles with sealed lid and hole were used. All measurements were carried out in a nitrogen gas flow of 50mL/minute. The heating rate was 10° C./minute unless indicated otherwise. Temperature and heat flow were calibrated via the melting peak of an indium reference. The measured data were evaluated with the software STARe V6.1.

On heating of all four polymorphs 1, 2, 3 and 4 of compound I in DSC experiments, their melting without preceding solid-solid transitions was observed. The following melting points were determined by heating samples of phases 1, 2, 3 and 4 with a heating rate of 10° C./minute to a temperature above the melting point.

|  | Melting point onset | Melting point peak |
|---|---|---|
| Phase 1 | 115.5° C. | 117.7° C. |
| Phase 2 | 117.2° C. | 119.0° C. |
| Phase 3 | 121.7° C. | 124.9° C. |
| Phase 4 | 118.2° C. | 120.6° C. |

Dynamic Vapor Sorption (DVS)

Moisture sorption/desorption isotherms were recorded on a DVS-1 from Surface Measurement Systems. Two cycles were run at 25° C., in which the relative humidity was stepwise increased and subsequently decreased again and the weight the sample was measured. The data were evaluated with the software DVSWin V. 2.15 With samples of phase 1, 2, 3 and 4 of compound I the following water uptake (in mass percent) as a function of the relative humidity was determined.

| Relative humidity | Phase 1 | Phase 2 | Phase 3 | Phase 4 |
|---|---|---|---|---|
| 20% | 0.00% | 0.04% | 0.02% | 0.05% |
| 40% | 0.01% | 0.05% | 0.03% | 0.02% |
| 60% | 0.01% | 0.09% | 0.06% | 0.15% |
| 80% | 1.36% | 1.79% | 0.30% | 1.80% |

Raman Spectroscopy

Figure 8:
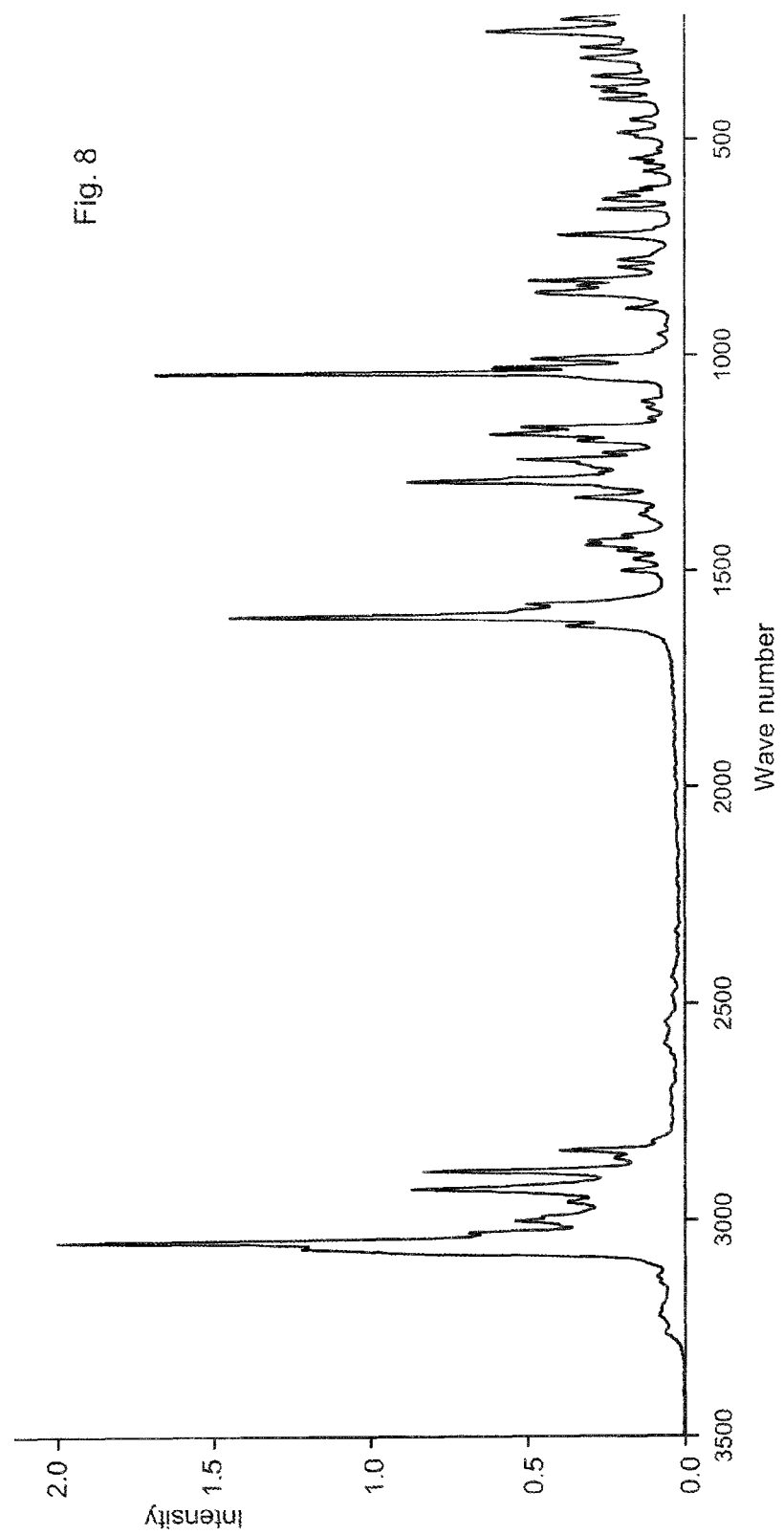
Figure 9:
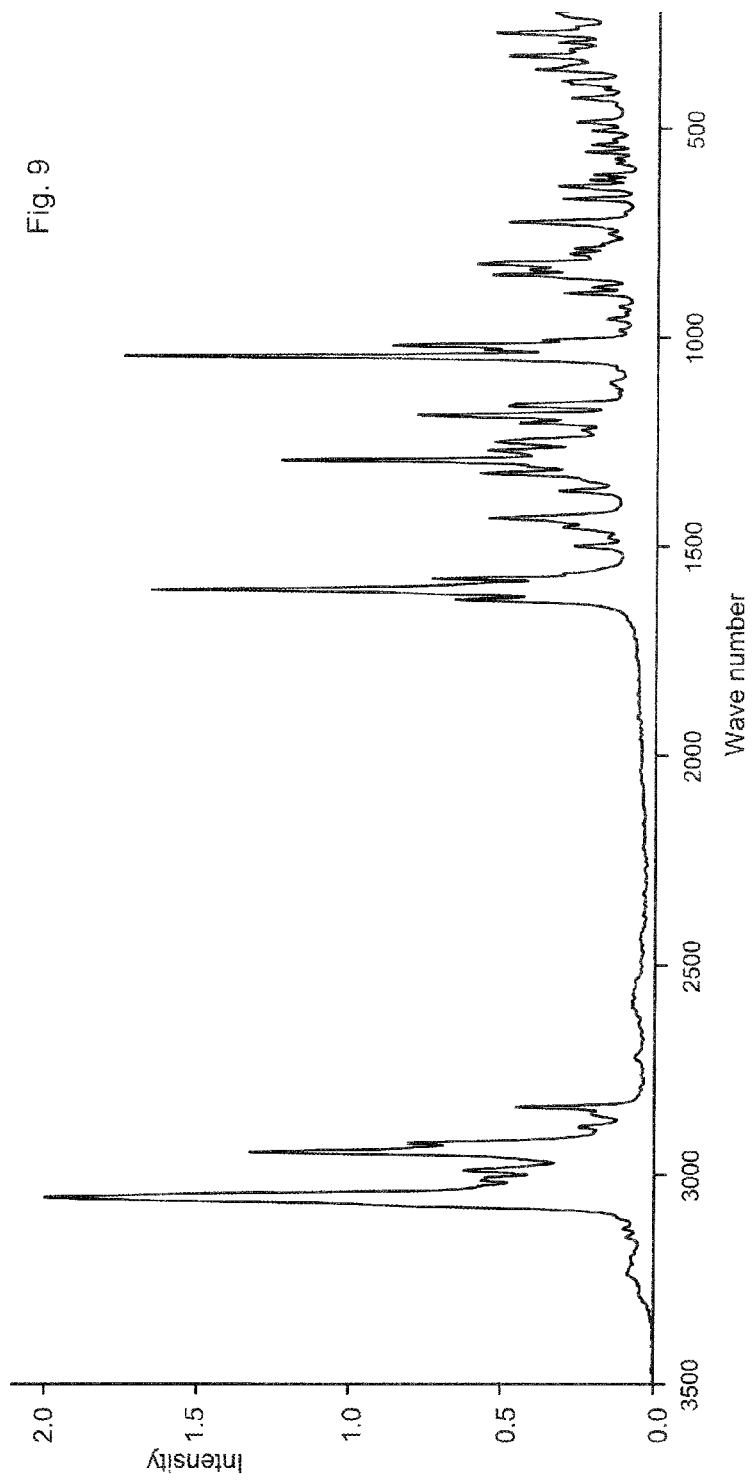
FIG. 9—FT Raman spectrum of polymorph 2of compound I in the wave number range from 3500to 200cm$^{-1}$(x-axis: wave number [cm$^{-1}$]; y-axis: intensity [arbitrary units]).
Figure 10:
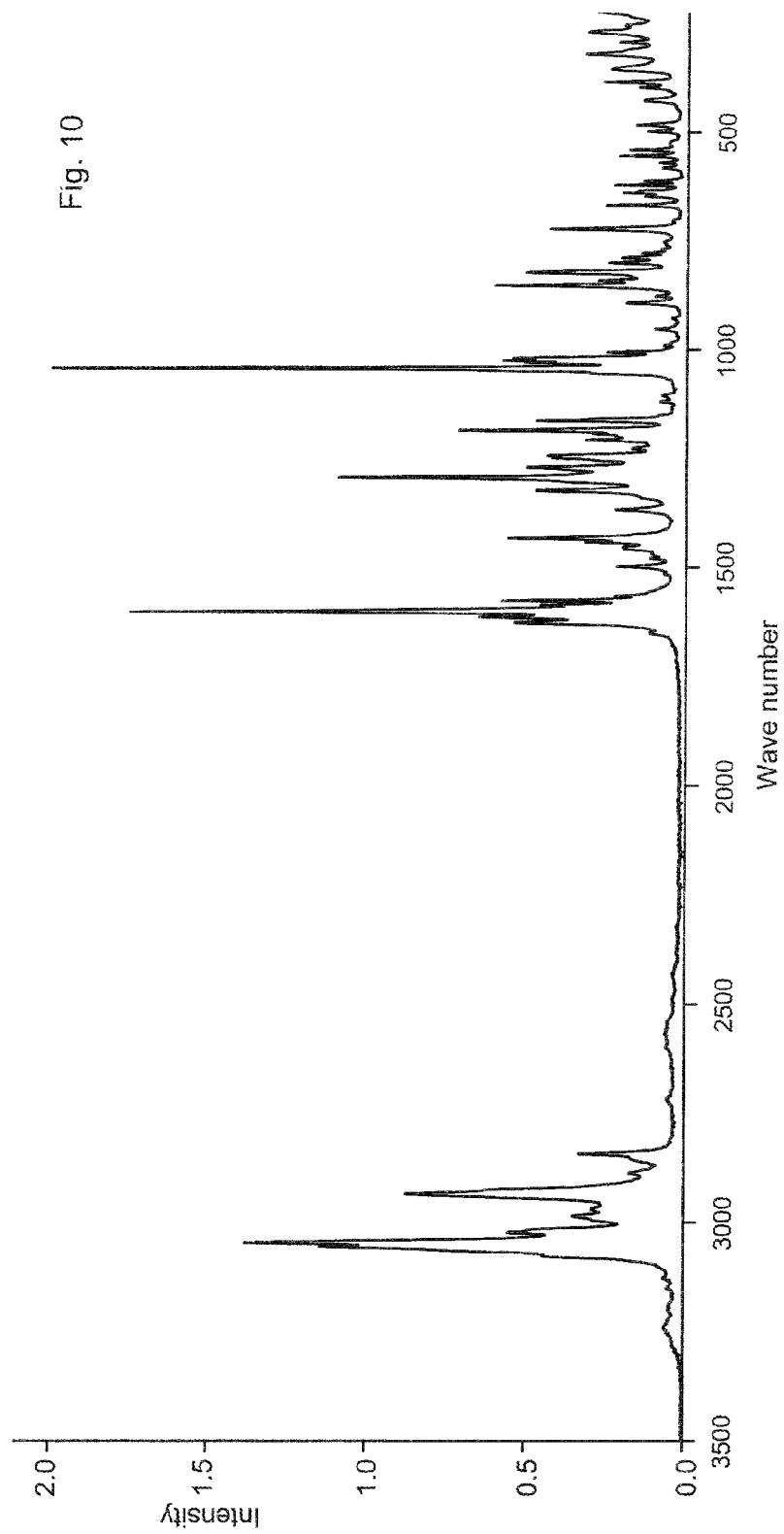
FIG. 10—FT Raman spectrum of polymorph 3of compound I in the wave number range from 3500to 200cm$^{-1}$(x-axis: wave number [cm$^{-1}$]; y-axis: intensity [arbitrary units]).
Figure 11:
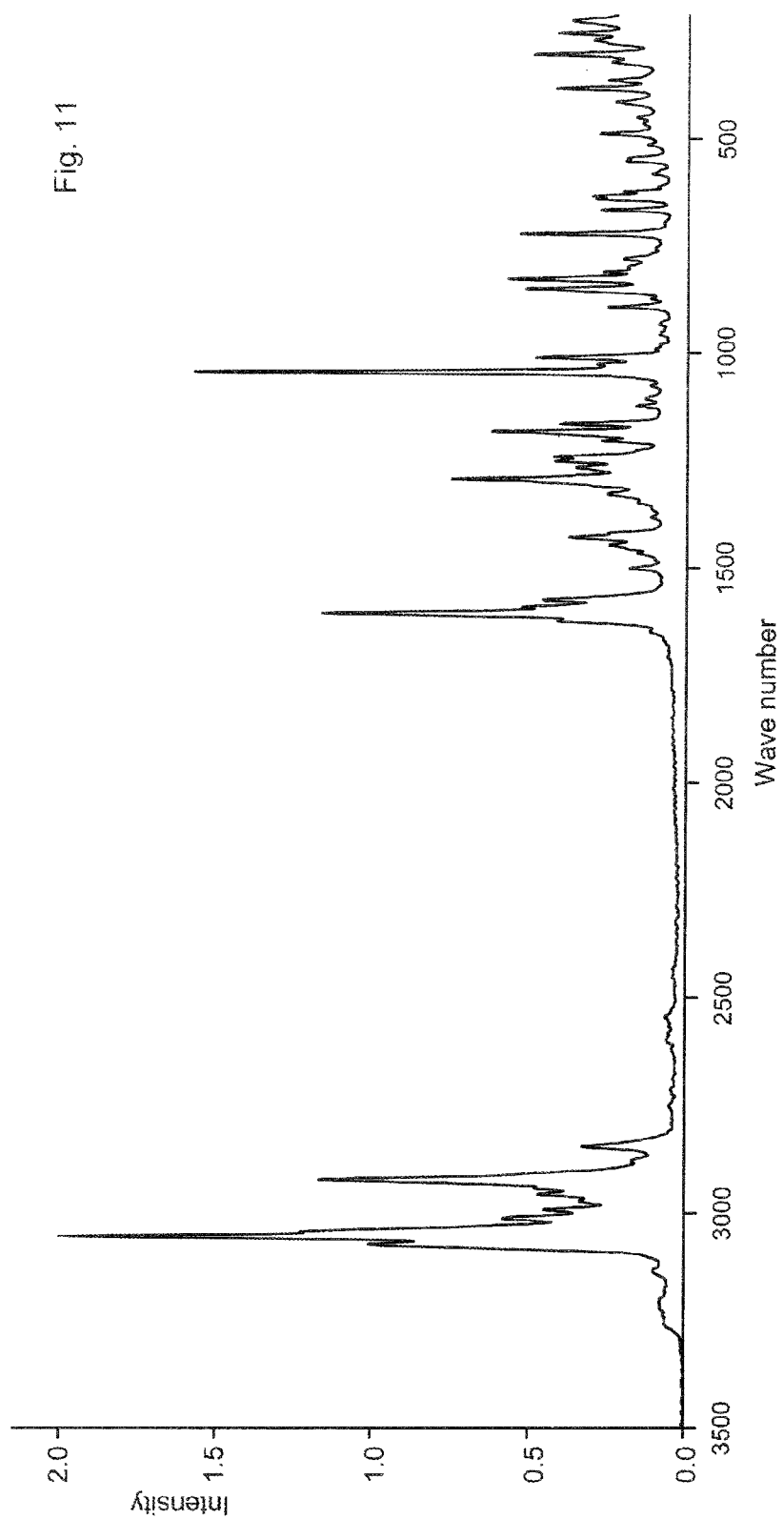
FIG. 11—FT Raman spectrum of polymorph 4of compound I in the wave number range from 3500to 200cm$^{-1}$(x-axis: wave number [cm$^{-1}$]; y-axis: intensity [arbitrary units]).
Figure 12:
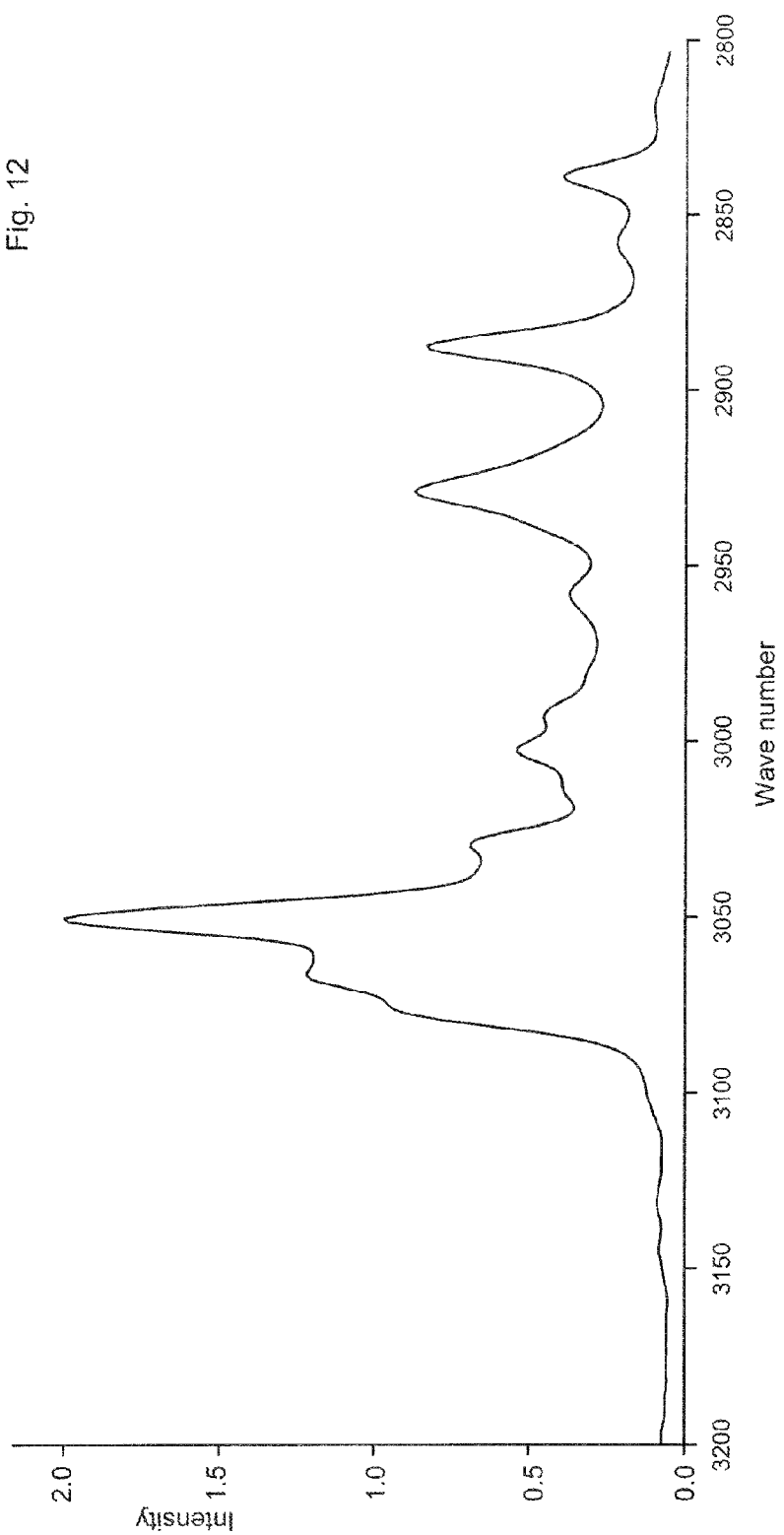
FIG. 12—FT Raman spectrum of polymorph 1of compound I in the wave number range from 3200to 2800cm$^{-1}$(x-axis: wave number [cm$^{-1}$]; y-axis: intensity [arbitrary units]).
Figure 13:
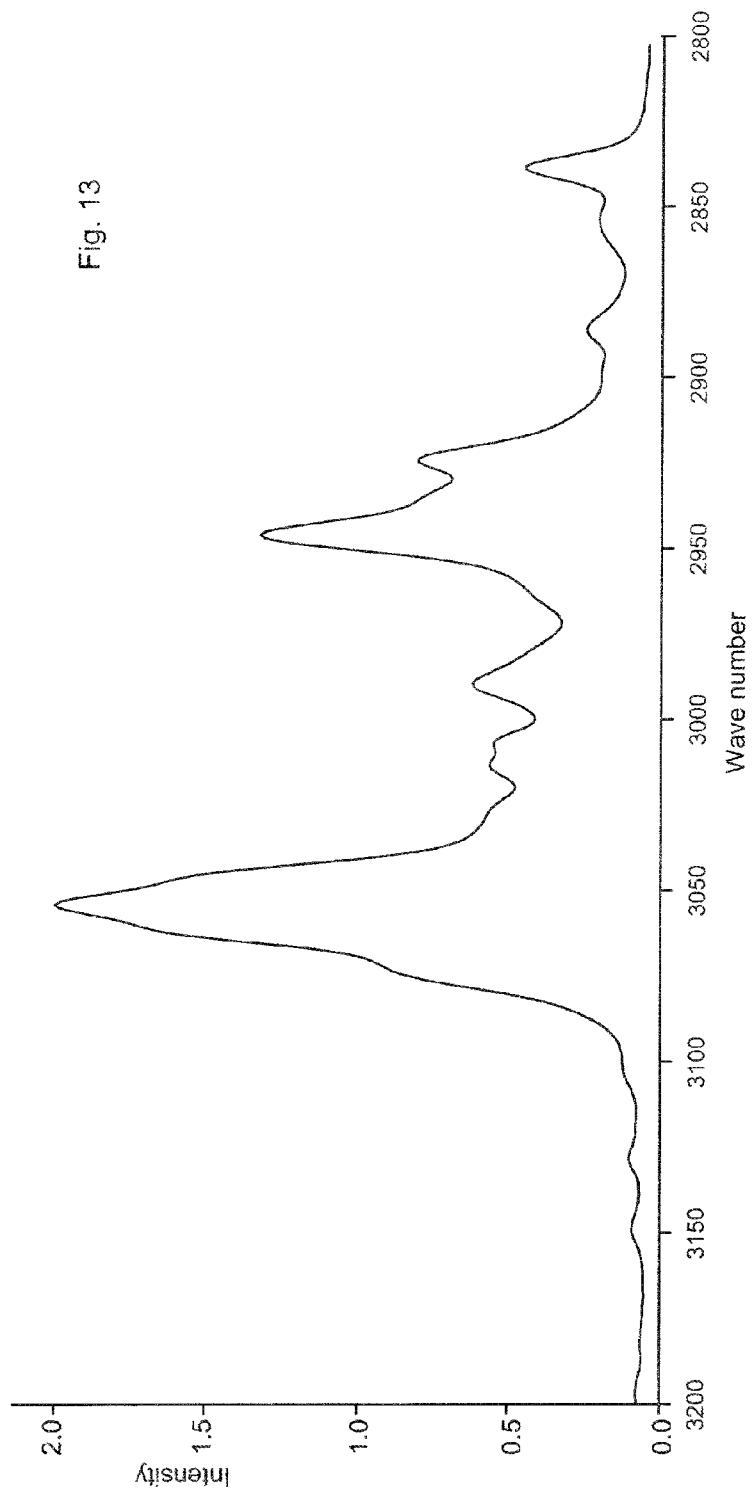
FIG. 13—FT Raman spectrum of polymorph 2of compound I in the wave number range from 3200to 2800cm$^{-1}$(x-axis: wave number [cm$^{-1}$]; y-axis: intensity [arbitrary units]).
Figure 14:
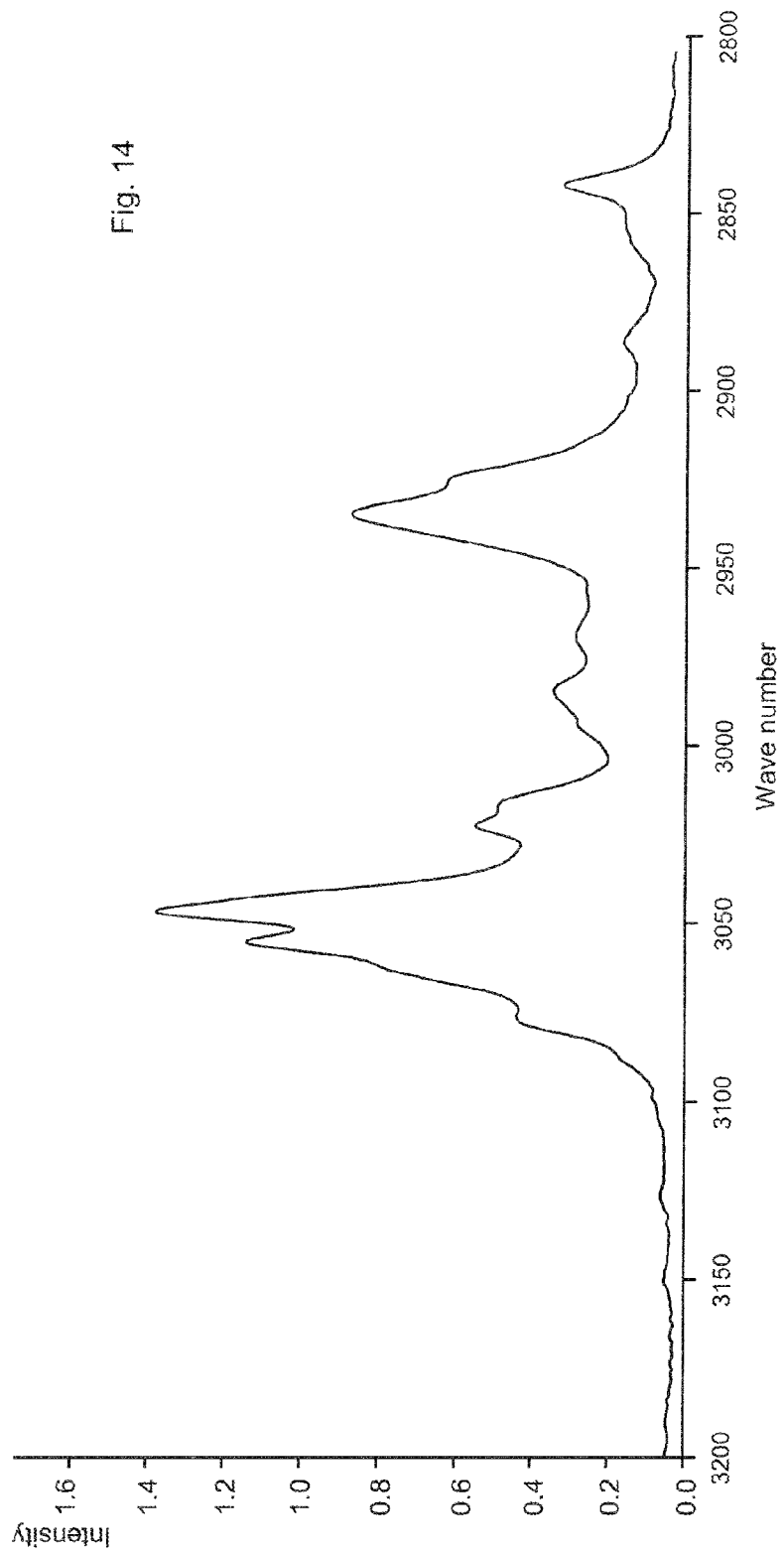
FIG. 14—FT Raman spectrum of polymorph 3of compound I in the wave number range from 3200to 2800cm$^{-1}$(x-axis: wave number [cm$^{-1}$]; y-axis: intensity [arbitrary units]).
Figure 15:
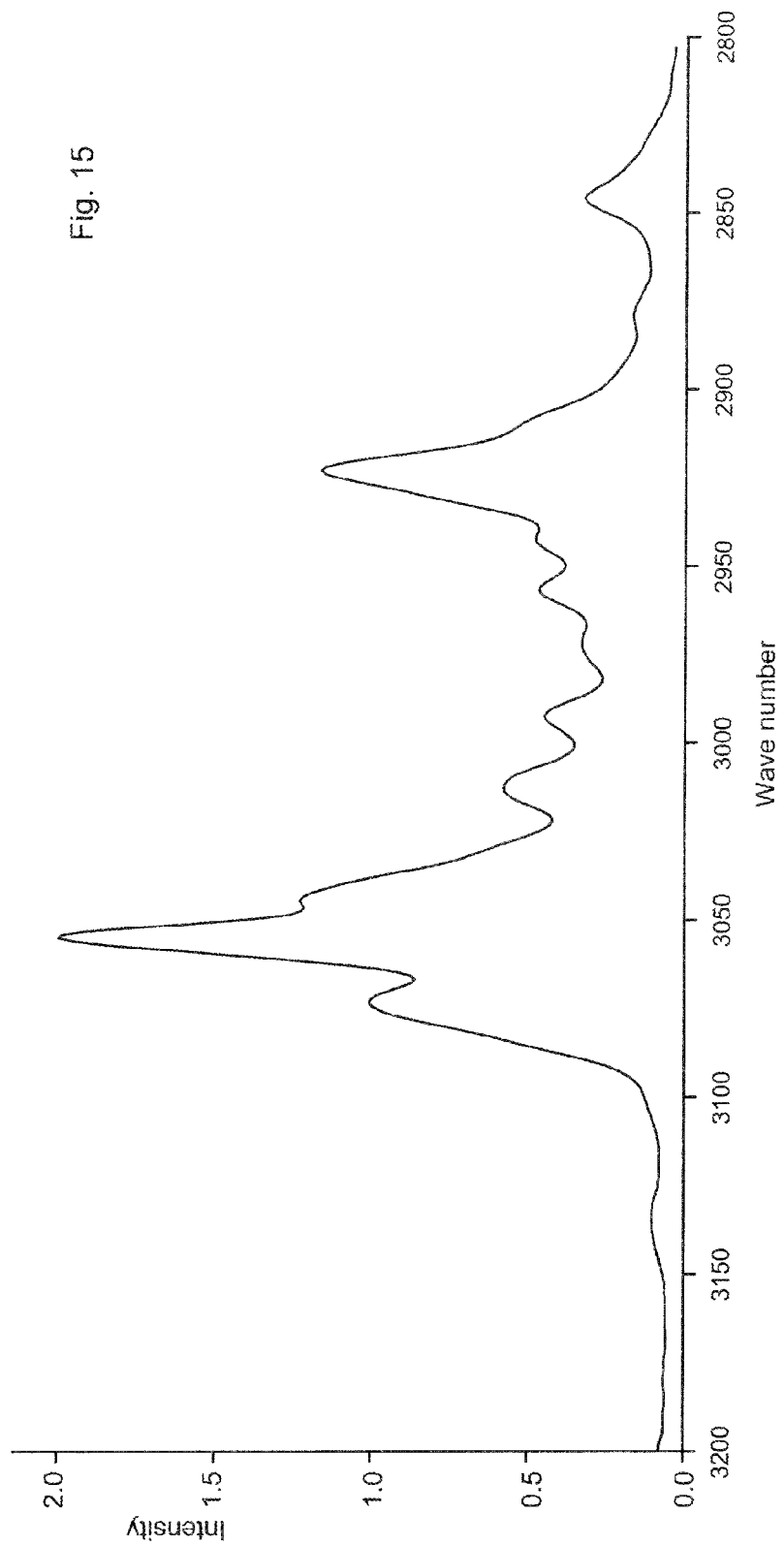
FIG. 15—FT Raman spectrum of polymorph 4of compound I in the wave number range from 3200to 2800cm$^{-1}$(x-axis: wave number [cm$^{-1}$]; y-axis: intensity [arbitrary units]).
Figure 16:
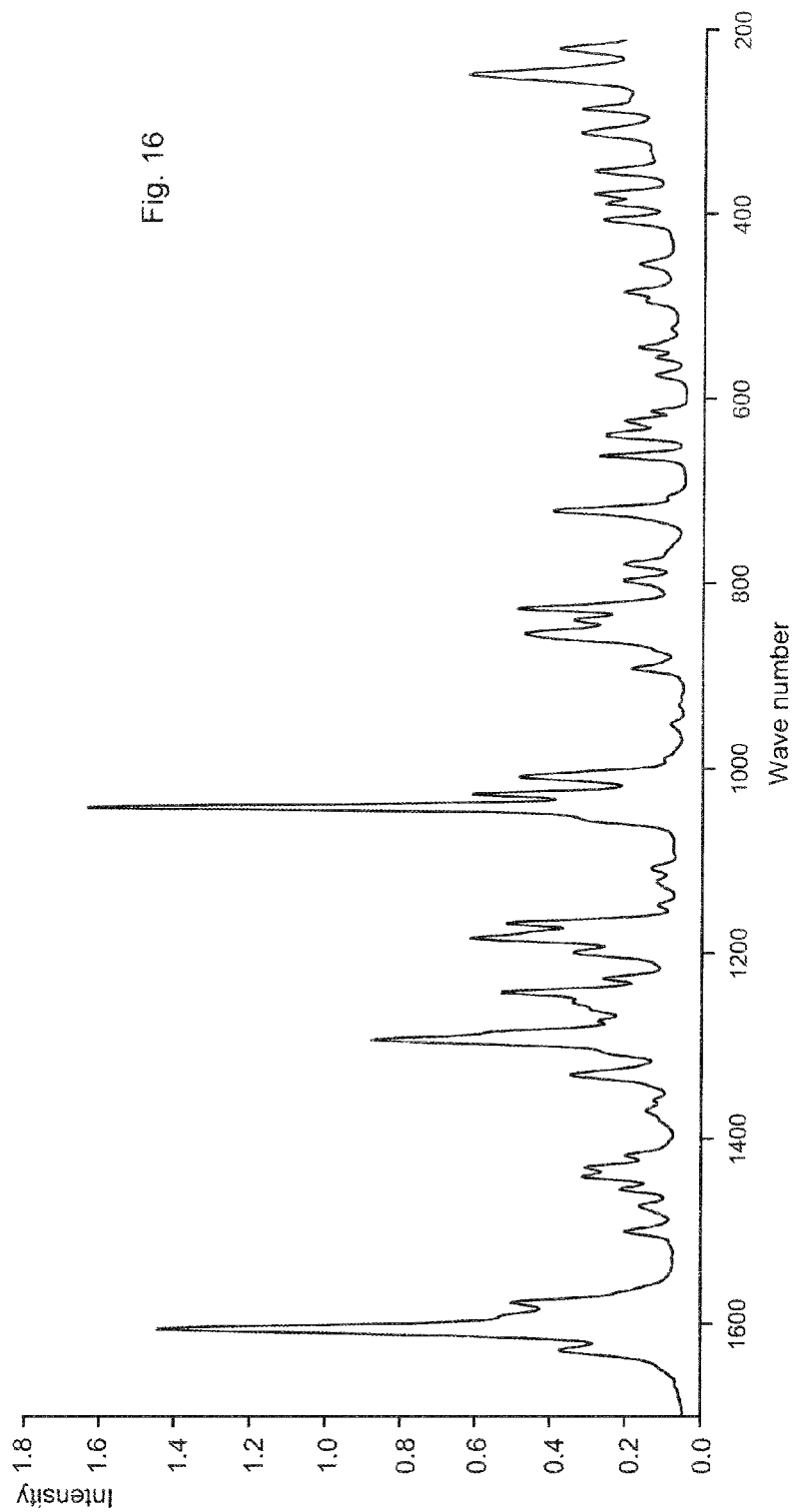
FIG. 16—FT Raman spectrum of polymorph 1of compound I in the wave number range from 1700to 200cm$^{-1}$(x-axis: wave number [cm$^{-1}$]; y-axis: intensity [arbitrary units]).
Figure 17:
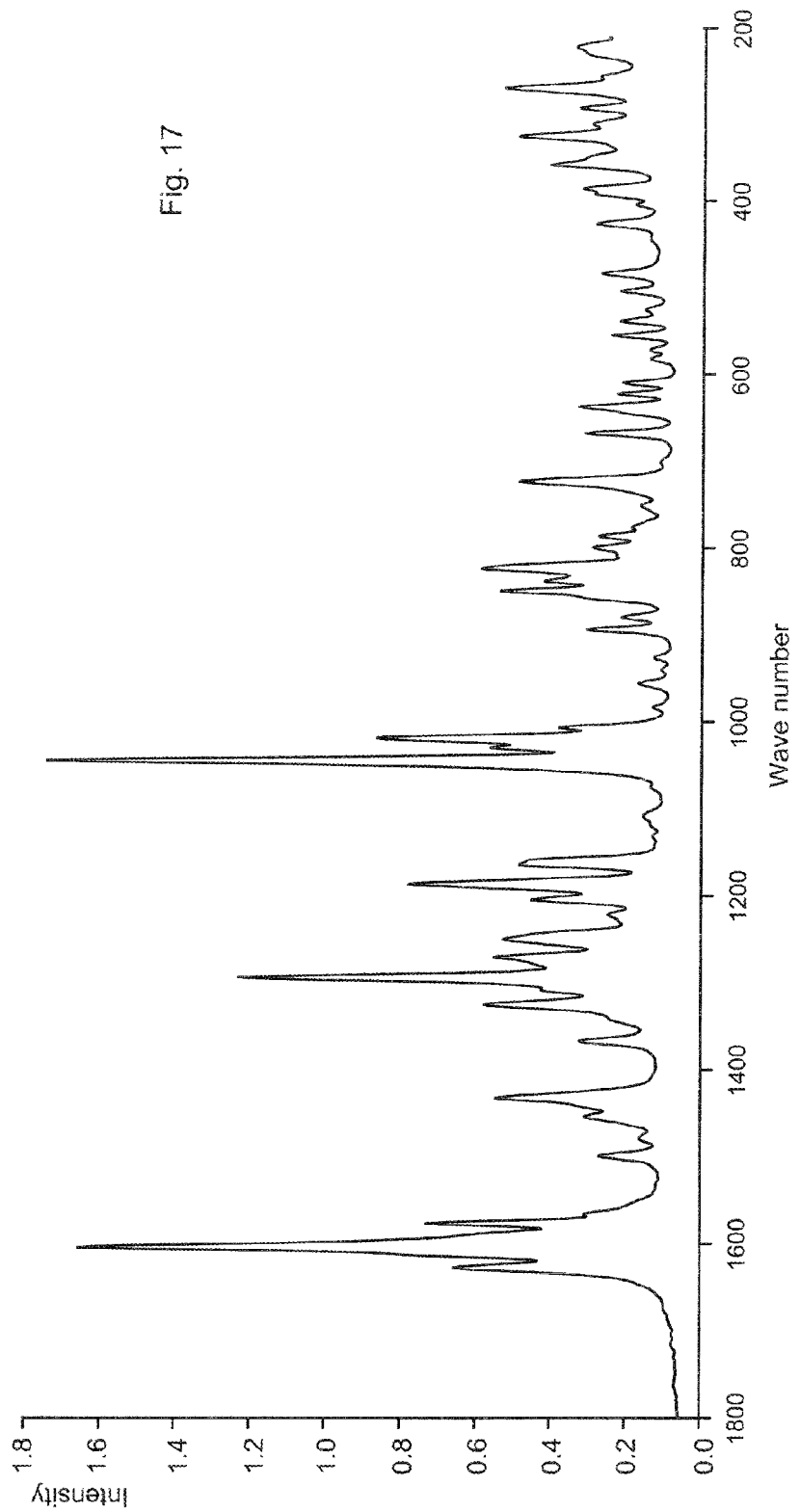
FIG. 17—FT Raman spectrum of polymorph 2of compound I in the wave number range from 1700to 200cm$^{-1}$(x-axis: wave number [cm$^{-1}$]; y-axis: intensity [arbitrary units]).
Figure 18:
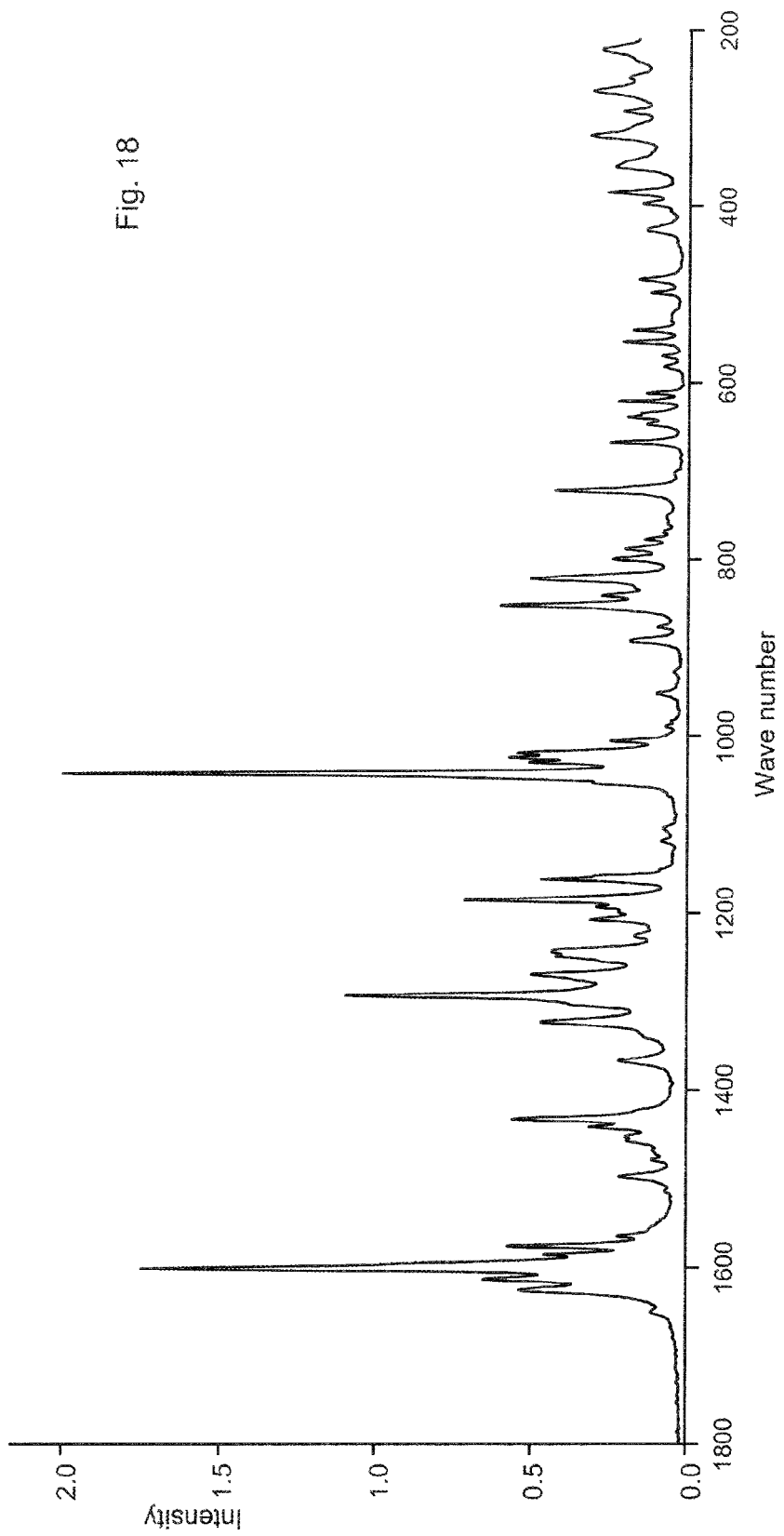
FIG. 18—FT Raman spectrum of polymorph 3of compound I in the wave number range from 1700to 200cm$^{-1}$(x-axis: wave number [cm$^{-1}$]; y-axis: intensity [arbitrary units]).

Raman spectra were recorded with an FT-Raman spectrometer (RFS100/S, Bruker) equipped with a 1.5W NIR-Laser (Nd:YAG; λ=1064nm) and a nitrogen-cooled D418-T NIR-Detector. The spectra were evaluated and plotted with the software OPUS V. 4.2 The observed Raman spectra of phases 1, 2, 3 and 4 of compound I are displayed in FIGS. 8 to 19. The wave numbers in $cm^{-1}$ of characteristic Raman signals are specified above.

Crystal Structures

The crystal structures of phases 1, 3 and 4 of compound I were determined by X-ray single crystal structure analysis. Single crystal X-ray diffraction data were collected at room temperature on a Bruker/AXS three circle diffractometer, equipped with a SMART APEX area detector, and a molybdenum $K_\alpha$ rotating anode generator, operated at 50kV/120mA and adjusted to a fine focus of $0.5 \times 5mm^2$ Phases 1 and 3 crystallize in the monoclinic space group $P2_1/c$ with one molecule in the asymmetric unit, while phase 4 crystallizes in the triclinic space group P-1 with also one molecule in the asymmetric unit. The unit cell of phase 3 was determined by indexation of the X-ray powder diffraction pattern (measured at room temperature). The data of the unit cells are given in Table 1

TABLE 1

Unit cell parameters of polymorphs 1, 2, 3 and 4 of compound I

| Phase | 1 | 2 | 3 | 4 |
|---|---|---|---|---|
| Crystal system | monoclinic | monoclinic | monoclinic | triclinic |
| Space group | $P2_1/c$ |  | $P2_1/c$ | P-1 |
| z | 4 | 4 | 4 | 2 |
| a [Å] | 11.31 ± 0.01 | 8.75 ± 0.01 | 8.81 ± 0.01 | 8.38 ± 0.01 |
| b [Å] | 8.44 ± 0.01 | 27.96 ± 0.01 | 15.24 ± 0.01 | 11.15 ± 0.01 |
| c [Å] | 26.86 ± 0.01 | 11.09 ± 0.01 | 20.11 ± 0.01 | 13.97 ± 0.01 |
| α [°] | 90.00 | 90.00 | 90.00 | 79.40 ± 0.01 |
| β [°] | 101.80 ± 0.01 | 102.26 ± 0.01 | 102.22 ± 0.01 | 85.19 ± 0.01 |
| γ [°] | 90.00 | 90.00 | 90.00 | 86.55 ± 0.01 |
| V [Å³] (1) | 2510.5 | 2651.2 | 2637.7 | 1277.1 |
| ρ [Mgm⁻³] (1) | 1.269 |  | 1.208 | 1.247 |

(1) calculated

Maturation Experiments

By maturation experiments (slurry conversion) in the temperature region from 0° C. to 80° C. the relative stability of the polymorphs of compound I was investigated.

Maturation experiments (a) to (d) were performed under the specified conditions, starting from a 1:1 mixture of polymorphs 1 and 4.

(a) The phase mixture was suspended in ethanol. After stirring the suspension for two days at 60° C., the solid was quickly isolated by vacuum filtration.

(b) The phase mixture was suspended in butyl acetate. After stirring the suspension for two days at 60° C., the solid was quickly isolated by vacuum filtration.

(c) The phase mixture was suspended in 1-pentanol. After stirring the suspension for four hours at 80° C., the solid was quickly isolated by vacuum filtration.

(d) The phase mixture was suspended in 1-octanol. After stirring the suspension for four hours at 80° C., the solid was quickly isolated by vacuum filtration.

In all maturation experiments (a) to (d) the solid had completely transformed to phase 1.

Maturation experiments (e) to (p) were performed by stirring the suspension under the specified conditions and isolating the solid by vacuum filtration, starting from polymorph 4.

(e) Maturation of 0.208g of compound I in 1.3ml of water/methanol (1:1) was performed at room temperature for four weeks. After 7 days the sample was seeded with a small amount of polymorph 1 and polymorph 2.

(f) Maturation of 0.209g of compound I in 1.0ml of water/ethanol (1:1) was performed at room temperature for four weeks. After 7 days the sample was seeded with a small amount of polymorph 1 and polymorph 2.

(g) Maturation of 0.238g of compound I in 1.4ml of acetone was performed at room temperature for four weeks. After 7 days the sample was seeded with a small amount of polymorph 1 and polymorph 2.

(h) Maturation of 0.218g of compound I in 0.9ml of methyl ethyl ketone was performed at room temperature for four weeks. After 7 days the sample was seeded with a small amount of polymorph 1 and polymorph 2.

(i) Maturation of 0.218g of compound I in 0.7ml of ethyl acetate was performed at room temperature for four weeks.

After 7days the sample was seeded with a small amount of polymorph 1and polymorph 2.
(j) Maturation of 0.207g of compound I in 0.7ml of butyl acetate at room temperature for four weeks. After 7days the sample was seeded with a small amount of polymorph 1and polymorph 2.
(k) Maturation of 0.204g of compound I in 0.7ml of tetrahydrofuran was performed at room temperature for four weeks. After 7days the sample was seeded with a small amount of polymorph 1and polymorph 2.
(l) Maturation of 0.208g of compound I in 0.4ml of 1,4-dioxane was performed at room temperature for four weeks. After 7days the sample was seeded with a small amount of polymorph 1and polymorph 2.
(m) Maturation of 0.204g of compound I in 0.7ml of acetonitrile was performed at room temperature for four weeks. After 7days the sample was seeded with a small amount of polymorph 1and polymorph 2.
(o) Maturation of 0.352g of compound I in 0.7ml of dichloromethane was performed at room temperature for four weeks. After 7days the sample was seeded with a small amount of polymorph 1and polymorph 2.
(p) Maturation of 0.223g of compound I in 0.6ml of was performed isobutanol at room temperature for four weeks. After 7days the sample was seeded with a small amount of polymorph 1and polymorph 2.

Maturation experiments (e) to (p) all yielded pure polymorph 1.

Further maturation experiments starting from phase mixtures consisting of polymorphs 1, 2and 4were performed analogously at 0° C., 20° C. and 40° C. All these experiments yielded pure polymorph 1.

The performed maturation experiments prove that among the known polymorphs phase 1is thermodynamically most stable in the investigated temperature range.

The invention claimed is:

1. A form of 2'-{[2-(4-methoxy-phenyl)-acetylamino]-methyl}-biphenyl-2-carboxylic acid(2-pyridin-3-yl-ethyl)-amide comprising polymorph 1 thereof.

2. The form of 2'-{[2-(4-methoxy-phenyl)-acetylamino]-methyl}-biphenyl-2-carboxylic acid (2-pyridin-3-yl-ethyl)-amide as claimed in claim 1, which is polymorph 1 and has at least one property of
(a) characteristic reflections in an X-ray powder diffractogram using $CuK_{\alpha 1}$ radiation in transmission mode at a 2θ angle [°] of 6.7±0.2, 13.2±0.2, 17.6±0.2, 19.1±0.2, 20.0±0.2, 21.4±0.2, and 22.5±0.2; and
(b) characteristic signals in an FT (Fourier-Transformation) Raman spectrum using a near infrared laser (λ=1064 nm) at 3050±2 $cm^{-1}$, 2929±2 $cm^{-1}$, 2887±2 $cm^{-1}$, 1605±2 $cm^{-1}$, 1293 ±2 $cm^{-1}$, and 1042±2 $cm^{-1}$.

3. A pharmaceutical composition comprising polymorphs 1 of 2'-{[2-(4-methoxy-phenyl)-acetylamino]-methyl}-biphenyl-2-carboxylic acid(2-pyridin-3-yl-ethyl)-amide according to claim 1 and one or more pharmaceutical acceptable excipients.

4. The pharmaceutical composition of claim 3, comprising a active agent in addition to polymorph 1 of 2'-{[2-(4-methoxy-phenyl)-acetylamino]-methyl}-biphenyl-2-carboxylic acid(2-pyridin-3-yl-ethyl)-amide.

5. A method of treating atrial arrhythmia or sleep-related respiratory disorders in a patient in need thereof comprising administering to said patient a therapeutically effective amount of the pharmaceutical composition of claim 3.

6. The method of claim 5, wherein the sleep-related respiratory disorder is sleep apnea.

7. A process for the preparation of polymorph 1 of 2'-{[2-(4-methoxy-phenyl)-acetylamino]-methyl}-biphenyl-2-carboxylic acid(2-pyridin-3-yl-ethyl)-amide according to claim 1, comprising the steps of
(a) suspending 2'-{[2-(4-methoxy-phenyl)-acetylamino]-methyl}-biphenyl-2-carboxylic acid(2-pyridin-3-yl-ethyl)-amide at room temperature in a solvent selected from the group consisting of methanol, ethanol, methanol/water, ethanol/water, methyl acetate, ethyl acetate, butyl acetate, methyl ethyl ketone, tetrahydrofuran, 1,4-dioxane, acetonitrile and methylene chloride to obtain a suspension;
(b) maintaining the suspension at room temperature to allow formation of polymorph 1 crystals; and
(c) isolating the precipitate of polymorph 1;
or
(a') suspending 2'-{[2-(4-methoxy-phenyl)-acetylamino]-methyl}-biphenyl-2-carboxylic acid(2-pyridin-3-yl-ethyl)-amide at room temperature in a solvent selected from the group consisting of ethanol and isopropanol to obtain a suspension;
(b') maintaining the suspension at a temperature of 0° C. to 45° C. to allow formation of polymorph 1 crystals; and
(c') isolating the precipitate of polymorph 1;
or
(a") suspending 2'-{[2-(4-methoxy-phenyl)-acetylamino]-methyl}-biphenyl-2-carboxylic acid(2-pyridin-3-yl-ethyl)-amide at room temperature in acetone to obtain a suspension;
(b") maintaining the suspension at a temperature of 15° C. to 40° C. to allow formation of polymorph 1 crystals;
(c") isolating the precipitate of polymorph 1;
or
(a''') dissolving 2'-{[2-(4-methoxy-phenyl)-acetylamino]-methyl}-biphenyl-2-carboxylic acid(2-pyridin-3-yl-ethyl)-amide in ethanol to obtain a solution;
(b''') rapid cooling of the solution to a temperature of 0° C.; and
(c''') isolating the precipitate of polymorph 1.

8. A process for the purification of polymorph 1 of 2'-{[2-(4-methoxy -phenyl)-acetylamino]-methyl}-biphenyl-2-carboxylic acid (2-pyridin-3-yl-ethyl)-amide comprising a crystallizing the isolated precipitate of polymorph 1 obtained from claim 7.

* * * * *

UNITED STATES PATENT AND TRADEMARK OFFICE
CERTIFICATE OF CORRECTION

PATENT NO. : 9,056,833 B2
APPLICATION NO. : 13/375363
DATED : June 16, 2015
INVENTOR(S) : Norbert Nagel et al.

Page 1 of 2

It is certified that error appears in the above-identified patent and that said Letters Patent is hereby corrected as shown below:

On the Title Page:

In the Abstract, item 57, line 3, please replace "(2-pyhdine-3-yl-ethyl)-amide" with -- (2-pyridin-3-yl-ethyl)-amide--.

In the Claims:

At column 19, claim number 1, lines 37-39, please replace "2'-{[2-(4-methoxy-phenyl)-acetylamino]-methyl}-biphenyl-2-carboxylic acid(2-pyridin-3-yl-ethyl)-amide" with --2'-{[2-(4-methoxy-phenyl)-acetylamino]-methyl}-biphenyl-2-carboxylic acid (2-pyridin-3-yl-ethyl)-amide--;

At column 19, claim number 3, line 52, please replace "polymorphs" with --polymorph--;

At column 19, claim number 3, lines 53-54, please replace "2'-{[2-(4-methoxy-phenyl)-acetylamino]-methyl}-biphenyl-2-carboxylic acid(2-pyridin-3-yl-ethyl)-amide" with --2'-{[2-(4-methoxy-phenyl)-acetylamino]-methyl}-biphenyl-2-carboxylic acid (2-pyridin-3-yl-ethyl)-amide--;

At column 19, claim number 4, line 58 to column 20, lines 1-2, please replace "2'-{[2-(4-methoxy-phenyl)-acetylamino]-methyl}-biphenyl-2-carboxylic acid(2-pyridin-3-yl-ethyl)-amide" with --2'-{[2-(4-methoxy-phenyl)-acetylamino]-methyl}-biphenyl-2-carboxylic acid (2-pyridin-3-yl-ethyl)-amide--;

At column 20, claim number 7, lines 9-11, please replace "2'-{[2-(4-methoxy-phenyl)-acetylamino]-methyl}-biphenyl-2-carboxylic acid(2-pyridin-3-yl-ethyl)-amide" with --2'-{[2-(4-methoxy-phenyl)-acetylamino]-methyl}-biphenyl-2-carboxylic acid (2-pyridin-3-yl-ethyl)-amide--;

Signed and Sealed this
Ninth Day of February, 2016

Michelle K. Lee
*Director of the United States Patent and Trademark Office*

CERTIFICATE OF CORRECTION (continued)
U.S. Pat. No. 9,056,833 B2

In the Claims:

At column 20, claim number 7, lines 13-15, please replace "2'-{[2-(4-methoxy-phenyl)-acetylamino]-methyl}-biphenyl-2-carboxylic acid(2-pyridin-3-yl-ethyl)-amide" with --2'-{[2-(4-methoxy-phenyl)-acetylamino]-methyl}-biphenyl-2-carboxylic acid (2-pyridin-3-yl-ethyl)-amide--;

At column 20, claim number 7, lines 25-27, please replace "2'-{[2-(4-methoxy-phenyl)-acetylamino]-methyl}-biphenyl-2-carboxylic acid(2-pyridin-3-yl-ethyl)-amide" with --2'-{[2-(4-methoxy-phenyl)-acetylamino]-methyl}-biphenyl-2-carboxylic acid (2-pyridin-3-yl-ethyl)-amide--;

At column 20, claim number 7, lines 34-36, please replace "2'-{[2-(4-methoxy-phenyl)-acetylamino]-methyl}-biphenyl-2-carboxylic acid(2-pyridin-3-yl-ethyl)-amide" with --2'-{[2-(4-methoxy-phenyl)-acetylamino]-methyl}-biphenyl-2-carboxylic acid (2-pyridin-3-yl-ethyl)-amide--;

At column 20, claim number 7, lines 42-44, please replace "2'-{[2-(4-methoxy-phenyl)-acetylamino]-methyl}-biphenyl-2-carboxylic acid(2-pyridin-3-yl-ethyl)-amide" with --2'-{[2-(4-methoxy-phenyl)-acetylamino]-methyl}-biphenyl-2-carboxylic acid (2-pyridin-3-yl-ethyl)-amide--;

At column 20, claim number 8, lines 48-50, please replace "2'-{[2-(4-methoxy -phenyl)-acetylamino]-methyl}-biphenyl-2-carboxylic acid (2-pyridin-3-yl-ethyl)-amide" with --2'-{[2-(4-methoxy-phenyl)-acetylamino]-methyl}-biphenyl-2-carboxylic acid (2-pyridin-3-yl-ethyl)-amide--.